(12) United States Patent
Gliner et al.

(10) Patent No.: US 7,353,064 B2
(45) Date of Patent: Apr. 1, 2008

(54) SYSTEMS AND METHODS FOR ENHANCING OR OPTIMIZING NEURAL STIMULATION THERAPY FOR TREATING SYMPTOMS OF MOVEMENT DISORDERS AND/OR OTHER NEUROLOGIC DYSFUNCTION

(75) Inventors: Bradford Evan Gliner, Sammamish, WA (US); Allen Wyler, Seattle, WA (US); Brad Fowler, Duvall, WA (US); W. Douglas Sheffield, Seattle, WA (US)

(73) Assignee: Northstar Neuroscience, Inc., Seattle, WA (US)

( * ) Notice: Subject to any disclaimer, the term of this patent is extended or adjusted under 35 U.S.C. 154(b) by 608 days.

(21) Appl. No.: 10/782,526

(22) Filed: Feb. 19, 2004

(65) Prior Publication Data

US 2004/0249422 A1 Dec. 9, 2004

Related U.S. Application Data

(63) Continuation-in-part of application No. 10/317,002, filed on Dec. 10, 2002, now Pat. No. 7,236,830.

(51) Int. Cl.
*A61N 1/00* (2006.01)
(52) U.S. Cl. ....................................... 607/45
(58) Field of Classification Search ............... 607/45
See application file for complete search history.

(56) References Cited

U.S. PATENT DOCUMENTS

| 2,716,226 A | 8/1955 | Jonas |
|---|---|---|
| 2,721,316 A | 10/1955 | Shaw |
| 3,628,193 A | 12/1971 | Collins |
| 3,650,276 A | 3/1972 | Burghele et al. |
| 3,850,161 A | 11/1974 | Liss |
| 3,918,461 A | 11/1975 | Cooper |
| 4,030,509 A | 6/1977 | Heilman et al. |
| 4,125,116 A | 11/1978 | Fischell |
| 4,140,133 A | 2/1979 | Kastrubin et al. |
| 4,214,804 A | 7/1980 | Little |
| 4,245,645 A | 1/1981 | Picard et al. |
| 4,308,868 A | 1/1982 | Jhabvala |
| 4,328,813 A | 5/1982 | Ray |
| 4,340,038 A | 7/1982 | McKean |
| 4,390,023 A | 6/1983 | Rise |

(Continued)

FOREIGN PATENT DOCUMENTS

DE 19750043 5/1999

(Continued)

OTHER PUBLICATIONS

U.S. Appl. No. 10/583,630, filed Jun. 20, 2006, Lozano.

(Continued)

*Primary Examiner*—Scott M. Getzow
(74) *Attorney, Agent, or Firm*—Perkins Coie LLP

(57) ABSTRACT

In one embodiment, a procedure directed toward enhancing neural stimulation therapy efficacy comprises acquiring coherence and/or silent period measurements to facilitate and/or effectuate determination of neural stimulation parameters corresponding to a treatment program, and/or modification of neural stimulation parameters associated with a treatment program in view of short-term changes in a patient's symptomatic state and/or persistent or lasting changes in a patient's neurofunctional condition.

45 Claims, 11 Drawing Sheets

U.S. PATENT DOCUMENTS

| | | |
|---|---|---|
| 4,431,000 A | 2/1984 | Butler et al. |
| 4,474,186 A | 10/1984 | Ledley et al. |
| 4,542,752 A | 9/1985 | Dehaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,869,255 A | 9/1989 | Putz |
| 4,903,702 A | 2/1990 | Putz |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,044,368 A | 9/1991 | Putz |
| 5,054,906 A | 10/1991 | Lyons |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons, III et al. |
| 5,269,303 A | 12/1993 | Wernicke et al. |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,441,528 A | 8/1995 | Chang et al. |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,674,264 A | 10/1997 | Carter et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski |
| 5,735,814 A | 4/1998 | Elsberry et al. |
| 5,750,376 A | 5/1998 | Weiss et al. |
| 5,752,979 A | 5/1998 | Benabid |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,603 A | 11/1998 | Kovacs et al. |
| 5,833,709 A | 11/1998 | Rise et al. |
| 5,843,148 A | 12/1998 | Gijsbers et al. |
| 5,843,150 A | 12/1998 | Dreessen et al. |
| 5,846,196 A | 12/1998 | Siekmeyer et al. |
| 5,865,842 A | 2/1999 | Knuth et al. |
| 5,871,517 A * | 2/1999 | Abrams et al. ............... 607/45 |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsh |
| 5,913,882 A | 6/1999 | King |
| 5,916,171 A | 6/1999 | Mayevsky |
| 5,925,070 A | 7/1999 | King et al. |
| 5,928,144 A | 7/1999 | Real |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,024,702 A | 2/2000 | Iversen |
| 6,026,326 A | 2/2000 | Bardy |
| 6,035,236 A | 3/2000 | Jarding et al. |
| 6,038,480 A | 3/2000 | Hrdlicka et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,095,148 A | 8/2000 | Shastri et al. |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,527 A | 10/2000 | Howard, III et al. |
| 6,128,537 A | 10/2000 | Rise |
| 6,128,538 A | 10/2000 | Fischell et al. |
| 6,134,474 A | 10/2000 | Fischell et al. |
| 6,152,143 A | 11/2000 | Edwards |
| 6,161,044 A | 12/2000 | Silverstone |
| 6,161,045 A | 12/2000 | Fischell et al. |
| 6,161,047 A | 12/2000 | King et al. |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,205,361 B1 | 3/2001 | Kuzma et al. |
| 6,210,417 B1 | 4/2001 | Baudino et al. |

| | | | | | | |
|---|---|---|---|---|---|---|
| 6,221,908 B1 | 4/2001 | Kilgard et al. | | 7,107,104 B2 | 9/2006 | Keravel et al. |
| 6,230,049 B1 | 5/2001 | Fischell et al. | | 7,110,820 B2 | 9/2006 | Tcheng et al. |
| 6,236,892 B1 | 5/2001 | Feler | | 7,146,217 B2 | 12/2006 | Firlik et al. |
| 6,246,912 B1 | 6/2001 | Sluijter et al. | | 7,149,586 B2 | 12/2006 | Greenberg et al. |
| 6,263,225 B1 | 7/2001 | Howard, III | | 7,184,840 B2 | 2/2007 | Stolz et al. |
| 6,280,462 B1 | 8/2001 | Hauser et al. | | 2002/0099412 A1 | 7/2002 | Fischell et al. |
| 6,301,493 B1 | 10/2001 | Marro et al. | | 2002/0138101 A1 | 9/2002 | Suda et al. |
| 6,304,787 B1 | 10/2001 | Kuzma et al. | | 2002/0169485 A1 | 11/2002 | Pless et al. |
| 6,319,241 B1 | 11/2001 | King et al. | | 2003/0074032 A1 | 4/2003 | Gliner |
| 6,339,725 B1 | 1/2002 | Naritoku et al. | | 2003/0078633 A1 | 4/2003 | Firlik et al. |
| 6,353,754 B1 | 3/2002 | Fischell et al. | | 2003/0088274 A1 | 5/2003 | Gliner et al. |
| 6,354,299 B1 | 3/2002 | Fischell et al. | | 2003/0097161 A1 | 5/2003 | Firlik et al. |
| 6,356,792 B1 | 3/2002 | Errico et al. | | 2003/0114886 A1 | 6/2003 | Gluckman et al. |
| 6,360,122 B1 | 3/2002 | Fischell et al. | | 2003/0125786 A1 | 7/2003 | Gliner et al. |
| 6,366,813 B1 | 4/2002 | DiLorenzo | | 2003/0130706 A1 | 7/2003 | Sheffield et al. |
| 6,375,666 B1 | 4/2002 | Mische | | 2003/0176901 A1 | 9/2003 | May |
| 6,405,079 B1 | 6/2002 | Ansarinia | | 2003/0187490 A1 | 10/2003 | Gliner |
| 6,418,344 B1 | 7/2002 | Rezai et al. | | 2003/0195602 A1 | 10/2003 | Boling |
| 6,427,086 B1 | 7/2002 | Fischell et al. | | 2004/0073270 A1 | 4/2004 | Firlik et al. |
| 6,456,886 B1 | 9/2002 | Howard, III et al. | | 2004/0082847 A1 | 4/2004 | McDermott |
| 6,459,936 B2 | 10/2002 | Fischell et al. | | 2004/0088024 A1 | 5/2004 | Firlik et al. |
| 6,463,328 B1 | 10/2002 | John | | 2004/0092809 A1 | 5/2004 | DeCharms |
| 6,464,356 B1 | 10/2002 | Sabel et al. | | 2004/0102828 A1 | 5/2004 | Lowry et al. |
| 6,466,822 B1 | 10/2002 | Pless | | 2004/0111127 A1 | 6/2004 | Gliner et al. |
| 6,473,639 B1 | 10/2002 | Fischell et al. | | 2004/0131998 A1 | 7/2004 | Marom et al. |
| 6,480,743 B1 | 11/2002 | Kirkpatrick et al. | | 2004/0138550 A1 | 7/2004 | Hartlep et al. |
| 6,484,059 B2 | 11/2002 | Gielen | | 2004/0158298 A1 | 8/2004 | Gliner et al. |
| 6,487,450 B1 | 11/2002 | Chen | | 2004/0176831 A1 | 9/2004 | Gliner et al. |
| 6,497,699 B1 | 12/2002 | Ludvig et al. | | 2004/0181263 A1 | 9/2004 | Balzer et al. |
| 6,499,488 B1 | 12/2002 | Hunter et al. | | 2004/0236388 A1 | 11/2004 | Gielen et al. |
| 6,505,075 B1 | 1/2003 | Weiner | | 2005/0004620 A1 | 1/2005 | Singhal et al. |
| 6,507,755 B1 | 1/2003 | Gozani et al. | | 2005/0015129 A1 | 1/2005 | Mische |
| 6,529,774 B1 | 3/2003 | Greene | | 2005/0021104 A1 | 1/2005 | DiLorenzo |
| 6,539,263 B1 | 3/2003 | Schiff et al. | | 2005/0021105 A1 | 1/2005 | Firlik et al. |
| 6,549,814 B1 | 4/2003 | Strutz et al. | | 2005/0021106 A1 | 1/2005 | Firlik et al. |
| 6,556,868 B2 | 4/2003 | Naritoku et al. | | 2005/0021107 A1 | 1/2005 | Firlik et al. |
| 6,569,654 B2 | 5/2003 | Shastri et al. | | 2005/0021118 A1 | 1/2005 | Genau et al. |
| 6,591,138 B1 | 7/2003 | Fischell et al. | | 2005/0033378 A1 | 2/2005 | Sheffield et al. |
| 6,597,954 B1 | 7/2003 | Pless et al. | | 2005/0070971 A1 | 3/2005 | Fowler et al. |
| 6,615,065 B1 | 9/2003 | Barrett et al. | | 2005/0075679 A1 | 4/2005 | Gliner et al. |
| 6,622,048 B1 | 9/2003 | Mann et al. | | 2005/0075680 A1 | 4/2005 | Lowry et al. |
| 6,631,295 B2 | 10/2003 | Rubinstein et al. | | 2005/0096701 A1 | 5/2005 | Donovan et al. |
| 6,633,780 B1 | 10/2003 | Berger | | 2005/0113882 A1 | 5/2005 | Cameron et al. |
| 6,647,296 B2 | 11/2003 | Fischell et al. | | 2005/0119712 A1 | 6/2005 | Shafer |
| 6,658,299 B1 | 12/2003 | Dobelle | | 2005/0154425 A1 | 7/2005 | Boveja et al. |
| 6,665,562 B2 | 12/2003 | Gluckman et al. | | 2005/0154426 A1 | 7/2005 | Boveja et al. |
| 6,684,105 B2 | 1/2004 | Cohen et al. | | 2005/0182453 A1 | 8/2005 | Whitehurst |
| 6,687,525 B2 | 2/2004 | Llinas et al. | | 2005/0228451 A1 | 10/2005 | Jaax et al. |
| 6,690,974 B2 | 2/2004 | Archer et al. | | 2006/0015153 A1 | 1/2006 | Gliner et al. |
| 6,708,064 B2 | 3/2004 | Rezai | | 2006/0106430 A1 | 5/2006 | Fowler et al. |
| 6,725,094 B2 | 4/2004 | Saberski | | 2006/0106431 A1 | 5/2006 | Wyler et al. |
| 6,731,978 B2 | 5/2004 | Olson et al. | | 2006/0129205 A1 | 6/2006 | Boveja et al. |
| 6,764,498 B2 | 7/2004 | Mische | | 2006/0173522 A1 | 8/2006 | Osorio |
| 6,782,292 B2 | 8/2004 | Whitehurst | | 2006/0217782 A1 | 9/2006 | Boveja et al. |
| 6,788,975 B1 | 9/2004 | Whitehurst et al. | | 2006/0241717 A1 | 10/2006 | Whitehurst et al. |
| 6,795,737 B2 | 9/2004 | Gielen et al. | | | | |
| 6,810,286 B2 | 10/2004 | Donovan et al. | | | FOREIGN PATENT DOCUMENTS | |
| 6,839,594 B2 | 1/2005 | Cohen et al. | | | | |
| 6,873,872 B2 | 3/2005 | Gluckman et al. | | EP | 0214527 | 3/1987 |
| 6,892,097 B2 | 5/2005 | Holsheimer | | EP | 0319844 | 6/1989 |
| 6,895,280 B2 | 5/2005 | Meadows et al. | | EP | 0998958 | 5/2000 |
| 6,898,464 B2 | 5/2005 | Edell et al. | | EP | 1145736 | 10/2001 |
| 6,907,296 B1 | 6/2005 | Doan et al. | | EP | 1180056 | 11/2003 |
| 6,934,580 B1 | 8/2005 | Osorio et al. | | WO | WO 87-07511 | 12/1987 |
| 6,944,497 B2 | 9/2005 | Stypulkowski | | WO | WO 94-07564 | 4/1994 |
| 6,944,501 B1 | 9/2005 | Pless | | WO | WO 95-21591 | 8/1995 |
| 6,959,215 B2 | 10/2005 | Gliner et al. | | WO | WO 97-45160 | 12/1997 |
| 6,990,377 B2 | 1/2006 | Gliner et al. | | WO | WO 98-06342 | 2/1998 |
| 7,006,859 B1 | 2/2006 | Osorio et al. | | WO | WO 01-97906 | 12/2001 |
| 7,010,351 B2 | 3/2006 | Firlik et al. | | WO | WO 02-09811 | 2/2002 |
| 7,024,247 B2 | 4/2006 | Gliner et al. | | WO | WO 02-36003 | 5/2002 |
| 7,065,412 B2 | 6/2006 | Swoyer | | WO | WO 02-38031 | 5/2002 |
| 7,107,097 B2 | 9/2006 | Stern et al. | | WO | WO 02-38217 | 5/2002 |

| | | |
|---|---|---|
| WO | WO 03-043690 | 5/2003 |
| WO | WO 03-082402 | 10/2003 |
| WO | WO 03-101532 | 12/2003 |

OTHER PUBLICATIONS

U.S. Appl. No. 11/254,060, filed Oct. 19, 2005, Wyler.
U.S. Appl. No. 11/254,240, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/583,349, filed Oct. 18, 2006, Sloan.
U.S. Appl. No. 11/638,326, filed Dec. 12, 2006, Gliner et al.
Barr, Deborah et al., "Induction and Reversal of Long-Term Potentiation by Low-and High-Intensity Theta Pattern Stimulation," The Journal of Neuroscience, 15(7): pp. 5402-5410 (Jul. 1995).
Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).
Behrens, T. et al., "Non-invasive mapping of connections between human thalamus and cortex using diffusion imaging," Nature neuroscience, vol. 6, No. 7, pp. 750-757 (Jul. 2003).
Bel, S. and Bauer, B.L., "Dorsal Column Stimulation (DCS): Cost to Benefit Analysis," Acta Neurochirurgica, Suppl. 52, pp. 121-123 (1991).
Benabid, A.L. et al., "Chronic electrical stimulation of the ventralis intermedius nucleus of the thalamus as a treatment of movement disorders," J. Neurosurg., Apr. 1997, 86(4); 737; http:-www.ncbi.nlm.nih.gov; [accessed Nov. 18, 2003].
Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.
Bezard et al., "Cortical Stimulation and Epileptic Seizure: A Study of the Potential Risk in Primates," Neurosurgery, vol. 45, No. 2, Aug. 1999, 346-350.
Binder, J. M.D., "Functional Magnetic Resonance Imaging: Language Mapping," Neurosurgery Clinics of North America, vol. 8, No. 3, Jul. 1997, pp. 383-392.
Bluestone, Avraham Y. et al., "Three-dimensional optical tomography of hemodynamics in the human head," Optics Express, vol. 9, No. 6, pp. 272-286 (Sep. 10, 2001).
Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].
Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation for Advanced Parkinson's Disease: Case Report," Movement Disorders, 15(1):169-171, 2000.
Cao, Yue et al., "Cortical Language Activation in Stroke Patients Recovering From Aphasia With Functional MRI," Stroke, vol. 30, pp. 2331-2340, Nov. 1999.
Cheun et al., "Differentiation of a Stem Cell Line Toward a Neuronal Phenotype," Int. J. Devl. Neuroscience, vol. 9, No. 4, pp. 391-404 (1991).
Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.
Cincotta et al., "Reorganization of the motor cortex in a patient with congenital hemiparesis and mirror movements," Neurology, vol. 55, pp. 129-131 (2000).
Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.
Classen et al., "Rapid Plasticity of Human Cortical Movement Representation Induced by Practice," The Journal of Neurophysiology, vol. 79, No. 2, pp. 1117-1123 (Feb. 1998).
CNN.com, Health, "Lab Zaps Strokes with Magnetic Pulses," http:/www.cnn.com/2004/HEALTH/conditions/11/29/zapping.strokes.ap/, Nov. 29, 2004, 4 pages [Retrieved on Dec. 2, 2004].
Cohen et al., "Studies of Neuroplasticity With Transcranial Magnetic Stimulation," The Journal of Clinical Neurophysiology, vol. 15, No. 4 (1998).
Cramer et al., "Use of Functional MRI to Guide Decisions in a clinical Stroke Trial," Stroke, Journal of the American Heart Association, May 2005, pp. e50-e52, American Heart Association, Dallas TX.
Cramer, S.C. and Bastings, E.P., "Mapping clinically relevant plasticity after stroke," Neuropharmacology vol. 19, No. 5, pp. 842-851 (Apr. 2000).
Cytokines Web Clinical Significance, Cytokines Web, 2 pages, URL: http:-cmbi.bjmu.edu.cn-cmbidata-cgf-CGF_Database-cytweb-roles-index.html [Retrieved on Sep. 2, 2005].
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
De Ridder, Dirk et al., "Magnetic and electrical stimulation of the auditory cortex for intractable tinnitus," Journal Neurosurg., vol. 100, pp. 560-564, (Mar. 2004).
Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.
Ding, Yuemin et al., "Neural Plasticity After Spinal Cord Injury," Current Pharmaceutical Design vol. 11, No. 11, pp. 1441-1450, Abstract Only, 1 page (Apr. 2005).
Duncan, Pamela W. et al., "Defining post-stroke recovery: implications for design and interpretation of drug trials," Neuropharmacology vol. 39, pp. 835-841 (2000).
Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.
Feys et al., "Value of somatosensory and motor evoked potentials in predicting arm recovery after a stroke," (Oct. 1999).
Franzini et al., "Reversal of thalamic hand syndrome by long-term motor cortex stimulation," Journal of Neurosurgery 93:873-875 (2000).
Fregni et al., "Antiepileptic Effects of Repetitve Transcranial Magnetic Stimulation in Patients with Cortical Malformations: An EEG and Clinical Study," ASSFN Proceedings 2004, Stereotactic and Functional Neurosurgery, 2005, 83:57-62.
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Gladstone et al., "Enhancing Recovery after Stroke with Noradrenergic Pharmacotherapy: A New Frontier?," Can J. Neurol. Sci., vol. 27, No. 2 (May 2000).
Gordon et al., "Parameters for direct cortical electrical stimulation in the human: histopathologic confirmation," Electroencephalography and clinical Neurophysiology, vol. 75, pp. 371-377 (1990).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Haglund, Michael M. et al., "Optical imaging of epileptiform and functional activity in human cerebral cortex," Nature, Aug. 20, 1992, pp. 668-671, vol. 358, Nature Publishing Group.
Hayakawa, Toshiji et al., "Changes in Cerebral Oxygenation and Hemodynamics During Obstructive Sleep Apneas," Chest, vol. 109, pp. 916-921 (1996).

Hodge, Jr., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., http://www.iss.com-Products-imagent_fmri.html, 1 page [Retrieved on Oct. 14, 2005].

Huang, Ying-Zu et al., "Theta Burst Stimulation of the Human Motor Cortex," Neuron, vol. 45, pp. 201-206 (Jan. 20, 2005).

Hummel, Friedheim et al., "Effects of non-invasive cortical stimulation on skilled motor function in chronic stroke," Brain Advance Access, pp. 1-10, (Jan. 5, 2005).

Imagent™ Functional Brain Imaging System, ISS, Inc., http://www.iss.com-Products-imagent.html, 2 pages [Retrieved on Oct. 14, 2005].

Imagent™ functional Near Infrared Imaging System (fNIRS) Brain Imaging Using Infrared Photons, ISS Inc., http://www.iss.com-products-imagent-imagent.pdf, 8 pages [Retrieved on Oct. 14, 2005].

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domains and Determinants of Quality of Life After Stroke Caused by Brian Infarction," Arch. Phys. Med. Rehabil., vol. 81, pp. 1541-1546 (Dec. 2000).

Kelly-Spratt, K. "Transfection of PC-12 cells: a model system for primary neuronal cells," Qiagen News, Customer application article, www.qiagen.com, Issue 4, 1998, 2 pages.

Keyvani, Kathy et al., "Suppression of proteasome C2 contralateral to ischemic lesions in rat brain," Brain Research, vol. 858, pp. 386-392, 2000.

Kilgard, Michael et al., "Cortical Map Reorganization Enabled by Nucleus Basalis Activity," Science, vol. 279 pp. 1714-1717 (Mar. 13, 1998).

Kimura, K. et al., "Electrically induced neurite outgrowth of PC12 cells on the electrode surface," Entrez PubMed, http://www.ncbi.nim.nih.gov/entrez/query.fcgi?db=pubmed&cmd=Retrieve&dopt=Abstract, 1 page.

Kinoshita et al., "Electric cortical stimulation suppresses eplieptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdúral Electrode Monitoring," Epilepsia 45(12):1560-1567, 2004, Blackwell Publishing, Inc.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias, BioChemistry of PD, http://www.mayo.edu-fdp-pd-info-dyskinesias.htm [Retrieved on Dec. 22, 2005].

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potentiation—A Decade of Progress?," Neuroscience, vol. 285, No. 5435, Issue of Sep. 17, 1999, pp. 1870-1874.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp. 181-191 (2004) Abstract Only- 1 page.

Martinez et al., "Motor hand recovery after stroke Prognostic yield of early transcranial magnetic stimulation," Electromyography. Clin. Neurophysiology, vol. 39, pp. 405-410 (1999).

Mendonca, A.C., "Directly applied low intensity direct electric current enhances peripheral nerve regeneration in rats," Journal of Neuroscience Methods, 2003, vol. 129, pp. 183-190.

Meyerson, B.A. et al., "Motor Cortex Stimulation as Treatment of Trigeminal Neuropathic Pain", Acta Neurochirurgica Supplementum, vol. 58, pp. 150-153 (1993).

Misawa et al., "Low-frequency transcranial magnetic stimulation for epilepsia partialis continua due to cortical dysplasia," Journal of the Neurological Sciences, vol. 234, 2005, pp. 37-39.

Montgomery, "Thalamic Stimulation," Neuroscience Pathways, The Cleveland Clinic Foundation, 2 pages.

Motamedi et al., "Optimizing Parameters for Terminating Cortical Afterdischarges with Pulse Stimulation," Epilepsia 43(8):836-846, 2002, Blackwell Publishing, Inc.

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp. 740-747, Dec. 1, 1999.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," http://www.public.asu.edu-~tmcdani-publications.htm, 5 pages [Retrieved on Dec. 22, 2005].

Pascual-Leone et al., "Study and Modulation of Human Cortical Excitability With Transcranial Magnetic Stimulation," Journal of Clinical Neurophysiology, 1998, vol. 15, No. 4, pp. 333-343.

Pascual-Leone et al., "Transcranial magnetic stimulation and neuroplasticity" Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," *Neuron*, vol. 45, pp. 181-183 (Jan. 20, 2005).

Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].

Politis, M. J., "Mammalian Optic Nerve Regeneration Following the Application of Electric Fields," *The Journal of Trauma*, Nov. 1988, vol. 28, No. 11, pp. 1548-1552.

Price, J. et al., "Neurotransplantation in neurodegenerative disease: a survey of relevant issues in development neurobiology," Novartis Foundation Symposium 231, 2000, pp. 148-165, Wiley, Chichester, UK.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

Schulz et al., "Localization of Epileptic Auras Induced on Stimulation by Subdural Electrodes," Epilepsia, Dec. 1997, vol. 38, Issue 12, pp. 1321-1329.

SCIRun, Scientific Computing and Imaging Institute. http://www.software.sci.utah.edu-scirun.html, 2 pages [Retrieved on Jul. 24, 2005].

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

Stefan et al., "Introduction of plasticity in the human motor cortex by paired associative stimulation," Brain, vol. 123, No. 3, pp. 572-584 (Mar. 2000).

Storer et al., "Microiontophoretic application of serotonin (5HT) 1B/1D agonists inhibits trigeminal cell firing in the cat," Brain, 1997, vol. 120, Issue 12, pp. 2171-2177, Oxford University Press.

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Taga, Gentaro et al., "Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 page [retrieved from the internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-Infrared study of fluctuations in cerebral hemodynamics during rest and motor stimulation: Temporal analysis and spatial mapping," Medical Physics, vol. 27, No. 4, pp. 801-815 (Apr. 2000).

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magentic stimulation during recovery of arm and hand function after stroke," Electroencephalography and Clinical Neurophysiology 101 pp. 316-328 (1996).

Turton, A. and Lemon, R.N., "The contributions of fast corticospinal input to the voluntary activation of proximal muscles in normal subjects and in stroke patients," Exp. Brain Res., vol. 129, pp. 559-572 (1999).

Vanderkooy et al., "Resolution Below the Least Significant Bit in Digital Systems with Dither," JAES, Mar. 1984, vol. 32, No. 3, pp. 106-113.

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of *Hippocampal foci*," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Rsearch, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.org, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Woodbury, D. et al., "Adult Rat and Human Bone Marrow Stromal Cells Differentiate into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience 18(3):1115-1123 (Feb. 1998).

U.S. Appl. No. 11/697,694, filed Apr. 6, 2007, Fowler.

U.S. Appl. No. 11/697,696, filed Apr. 6, 2007, Pascual-Leone.

U.S. Appl. No. 11/697,703, filed Apr. 6, 2007, Gaw.

* cited by examiner

SYSTEMS AND METHODS FOR ENHANCING OR OPTIMIZING NEURAL STIMULATION THERAPY FOR TREATING SYMPTOMS OF MOVEMENT DISORDERS AND/OR OTHER NEUROLOGIC DYSFUNCTION

CROSS-REFERENCE TO RELATED APPLICATION(S)

The present disclosure is a Continuation-in-Part of U.S. application Ser. No. 10/317,002, filed on Dec. 10, 2002 now U.S. Pat. No. 7,236,830.

TECHNICAL FIELD

The present disclosure relates generally to systems and methods for treating symptoms of Parkinson's Disease, other movement disorders, and/or other types of neurologic dysfunction. More particularly, the present disclosure describes a system and method for enhancing or optimizing the effectiveness of neural stimulation in treating the symptoms of movement disorders such as Parkinson's Disease and/or other types of neurologic dysfunction.

BACKGROUND

A wide variety of mental and physical processes are controlled or influenced by neural activity in particular regions of the brain. For example, various physical or cognitive functions are directed or affected by neural activity within the sensory or motor cortices. Across most individuals, particular areas of the brain appear to have distinct functions. In the majority of people, for example, the areas of the occipital lobes relate to vision; the regions of the left interior frontal lobes relate to language; portions of the cerebral cortex appear to be consistently involved with conscious awareness, memory, and intellect; and particular regions of the cerebral cortex as well as the basal ganglia, the thalamus, and the motor cortex cooperatively interact to facilitate motor function control.

Many problems or abnormalities with body functions can be caused by damage, disease, and/or disorders in the brain. For example, Parkinson's Disease (PD) is related to the degeneration or death of dopamine producing neurons in the substantia nigra region of the basal ganglia in the brain. Dopamine is neurotransmitter that transmits signals between areas of the brain. As the neurons in the substantia nigra deteriorate, the reduction in dopamine causes abnormal neural activity that results in a chronic, progressive deterioration of motor function control. Conservative estimates indicate that PD may affect more than one million individuals in the United States alone.

PD patients typically exhibit one or more of four primary symptoms. One primary symptom is a tremor in an extremity (e.g., a hand) that occurs while the extremity is at rest. Other primary symptoms include a generalized slowness of movement (bradykinesia); increased muscle rigidity or stiffness (rigidity); and gait or balance problems (postural dysfunction). In addition to or in lieu of these primary symptoms, PD patients may exhibit secondary symptoms including: difficulty initiating or resuming movements; loss of fine motor skills; lack of arm swing on the affected side of the body while walking; foot drag on the affected side of the body; decreased facial expression; voice and/or speech changes; cognitive disorders; feelings of depression or anxiety; and/or other symptoms.

Effectively treating PD or other movement disorders related to neurological conditions can be very difficult. Current treatments for PD symptoms include drugs, ablative surgical intervention, and/or neural stimulation. Drug treatments or therapies may involve, for example, the administration of a dopamine precursor that is converted to dopamine within the central nervous system (i.e., Levodopa (L-dopa)). Other types of drug therapies are also available. Unfortunately, drug therapies frequently become less effective or ineffective over time for an undesirably large patient population. A PD patient may require multiple drugs in combination to extend the time period of efficacy of drug therapies. Drug treatments additionally have a significant likelihood of inducing undesirable physical side effects; motor function complications such as uncontrollable involuntary movements (dyskinesias) are a particularly common side effect. Furthermore, drug treatments may induce undesirable cognitive side effects such as confusion and/or hallucinations.

Ablative surgical intervention for PD typically involves the destruction of one or more neural structures within the basal ganglia or thalamus that have become overactive because of the lack of dopamine. Unfortunately, such neural structures reside deep within the brain, and hence ablative surgical intervention is a very time consuming and highly invasive procedure. Potential complications associated with the procedure include risk of hemorrhage, stroke, and/or paralysis. Moreover, because PD is a progressive disease, multiple deep brain surgeries may be required as symptoms progressively worsen over time. Although ablative surgical intervention may improve a PD patient's motor function, it is not likely to completely restore normal motor function. Furthermore, since ablative surgical intervention permanently destroys neural tissue, the effects of such intervention cannot be readily adjusted or "fine tuned" over time.

Neural stimulation treatments have shown promising results for reducing some of the symptoms associated with PD. Neural activity is governed by electrical impulses or "action potentials" generated in and propagated by neurons. While in a quiescent state, a neuron is negatively polarized and exhibits a resting membrane potential that is typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials in the event that the integration exceeds a threshold potential. A neural firing threshold, for example, may be approximately −55 mV. Action potentials propagate to the neuron's synapses and are then conveyed to other synaptically connected neurons.

Neural activity in the brain can be influenced by neural stimulation, which involves the application of electrical and/or magnetic stimuli to one or more target neural populations within a patient using a waveform generator or other type of device. Various neural functions can thus be promoted or disrupted by applying an electrical current to one or more regions of the brain. As a result, researchers have attempted to treat certain neurological conditions, including PD, using electrical or magnetic stimulation signals to control or affect brain functions.

Deep Brain Stimulation (DBS) is a stimulation therapy that has been used as an alternative to drug treatments and ablative surgical therapies. In DBS, one or more electrodes are surgically implanted into the brain proximate to deep brain or subcortical neural structures. For treating PD or other movement disorders, the electrodes are positioned in or proximate to the ventrointermediate nucleus of the thalamus; basal ganglia structures such as the globus pallidus internalis (GPi); or the Subthalamic Nucleus (STN). The location of the stimulation site for the electrodes depends upon the symptoms that a patient exhibits and the severity of the symptoms.

In a typical DBS system, a pulse generator delivers a continuous or essentially continuous electrical stimulation signal having a pulse repetition frequency of approximately 100 Hz to each of two deep brain electrodes. The electrodes are bilaterally positioned on the left and right sides of the brain relative to particular neural structures such as those indicated above. U.S. Pat. No. 5,883,709 discloses one conventional DBS system for treating movement disorders.

Although DBS therapies may significantly reduce one or more PD symptoms, particularly when combined with drug treatments, they are highly invasive procedures. In general, configuring a DBS system to properly function within a patient requires two time consuming, highly invasive surgical procedures for implanting the DBS electrodes. Each such surgical procedure has essentially the same risks as those described above for ablative surgical intervention. Moreover, DBS may not provide relief from some movement disorders.

Motor Cortex Stimulation (MCS) is another type of brain stimulation treatment that has been proposed for treating Parkinson's Disease. MCS involves the application of stimulation signals to the motor cortex of a patient. One MCS system includes a pulse generator connected to a strip electrode that is surgically implanted over a portion of only the motor cortex (precentral gyrus). The use of MCS to treat PD symptoms is described in Canavero, Sergio, *Extradural Motor Cortex Stimulation for Advanced Parkinson's Disease: Case Report*, Movement Disorders (Vol. 15, No. 1, 2000).

Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating PD symptoms. Present MCS techniques, however, fail to address or adequately consider a variety of factors that may enhance or optimize the extent to which a patient experiences short term and/or long term relief from PD symptoms.

DETAILED DESCRIPTION

Figure 1:
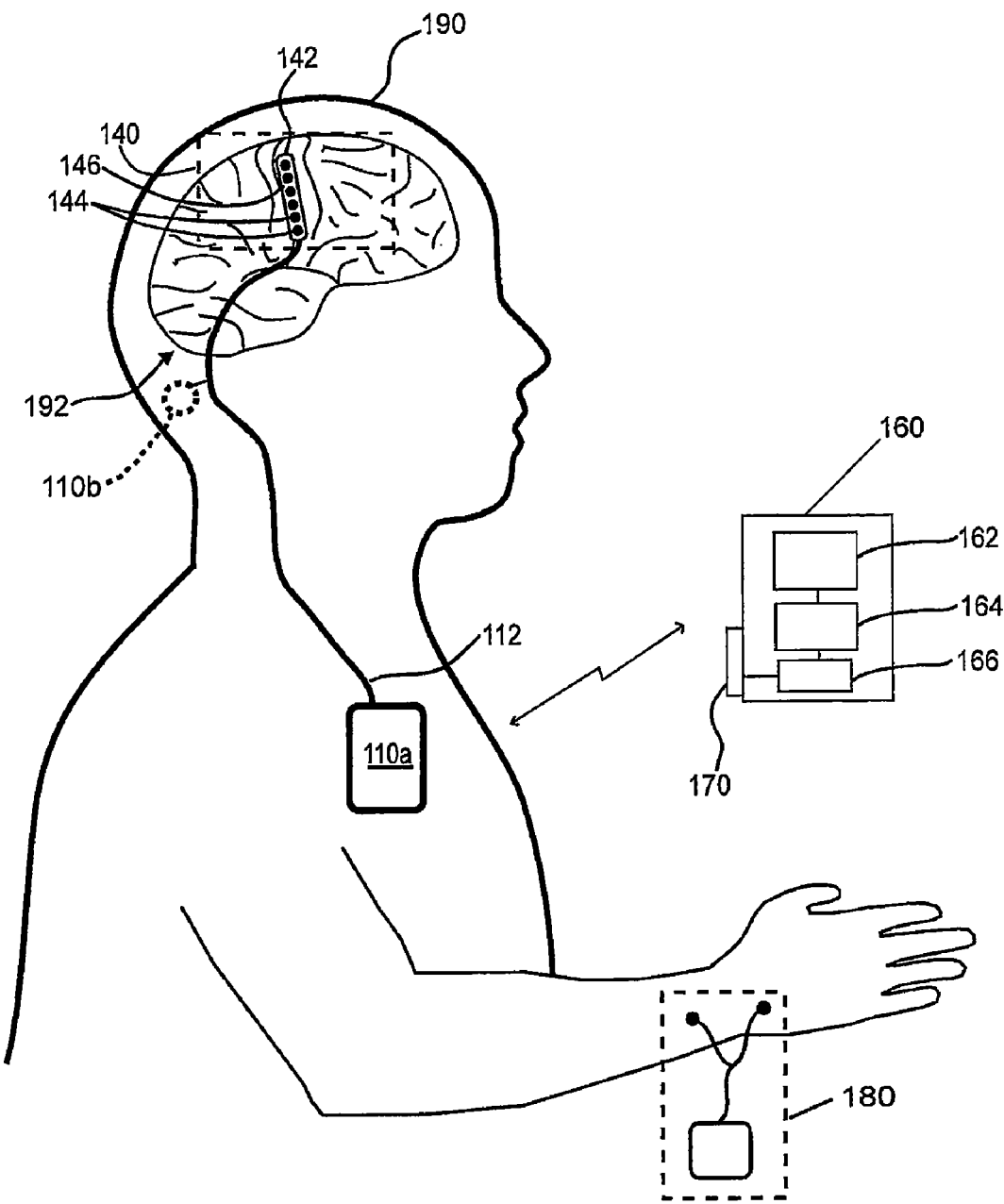
FIG. 1 is a schematic illustration of a neural stimulation system for treating symptoms of Parkinson's Disease and/or other neurological disorders according to an embodiment of the invention.

The following disclosure describes neural stimulation systems and methods for enhancing or optimizing the extent to which a patient may experience relief and/or functional recovery from deficits or symptoms associated with Parkinson's Disease (PD), other movement or motor disorders, and/or various other types of neurologic dysfunction or neurological disorders that may have one or more types of symptoms. Such symptoms may include, for example, tremor, rigidity, bradykinesia, postural dysfunction, spasticity, other motor deficits, speech deficits, visual disturbances, olfactory deficits, cognitive deficits, memory deficits, emotional or psychiatric disturbances, paresis, pain and/or other symptoms.

Different symptoms may respond to neural stimulation in different manners, and/or across different time scales. For example, neural stimulation optimized to beneficially affect tremor and/or rigidity to a significant degree may provide less significant or minimal benefit relative to other symptoms such as postural dysfunction. Additionally, neural stimulation that has a nearly immediate or reasonably rapid effect upon tremor and/or rigidity may have a significantly or greatly delayed effect upon other symptoms such as bradykinesia. Particular systems and/or methods described herein may facilitate enhancement or optimization of neural stimulation therapy for treating multiple patient symptoms that may exhibit different treatment response characteristics and/or different response timeframes.

Neural stimulation applied in accordance with various embodiments of the invention may give rise to one or more persistent, semi-persistent, and/or cumulative neurofunctional effects and/or may facilitate and/or effectuate neuroplastic changes within a patient's brain (e.g., within one or more cortical regions). Depending upon the nature of a patient's neurologic dysfunction, patient condition, patient treatment history, and/or embodiment details, one or more of such effects and/or changes may be permanent, essentially permanent, lasting, generally lasting, persistent, and/or somewhat persistent in the absence of neural stimulation. Additionally or alternatively, one or more of such effects and/or changes may exist for a limited time interval after neural stimulation is interrupted or discontinued, possibly such that the interval increases in duration over the course of a treatment program. The aforementioned types of effects and/or changes may additionally exist in the absence of neural stimulation even when one or more portions of a drug-related therapy are scaled back, compositionally modified, interrupted, discontinued, and/or otherwise adjusted.

Exemplary manners of applying or delivering neural stimulation to facilitate and/or effectuate cumulative neurofunctional effects and/or neuroplastic changes are described in U.S. application Ser. No. 09/802,808, entitled "Methods and Apparatus for Effectuating a Lasting Change in a Neural-Function of a Patient," filed on Mar. 8, 2001, which is incorporated herein by reference. Persistent or cumulative effects and/or neuroplastic changes may arise from adaptive structural changes or reorganizations in particular brain regions, which may result in enhancement, restoration, and/or development of one or more functional abilities (i.e., physical, sensory, and/or cognitive functions) associated with such brain regions, possibly on a long term or lasting basis. Application of neural stimulation to a patient in accordance with the principles described herein may increase the likelihood that persistent or cumulative neurofunctional effects and/or neuroplastic changes can occur to facilitate at least partial recovery of diminished or lost functionality associated with or giving rise to one or more patient symptoms. Such functional recovery may itself reduce the extent to which the patient requires neural stimulation and/or other therapy on an ongoing basis.

FIG. 1 is a schematic illustration of a neural stimulation system 100 for treating symptoms of PD and/or other disorders according to an embodiment of the invention. In one embodiment, the neural stimulation system 100 comprises a pulse generator 110a configured to deliver stimulation signals to a patient 190 using a set of electrodes 140. The pulse generator 110a may be coupled to the set of electrodes 140 by one or more leads 112. The pulse generator 110a may further be configured for wireless and/or wire-based communication with one or more programming units 160, 161. Depending upon embodiment details, the system 100 may further include one or more patient monitoring units 180 configured to detect, monitor, indicate, measure, and/or assess the severity of particular types of patient symptoms or deficits.

The set of electrodes 140 may include one or more cortical electrodes 142 configured to provide, deliver, and/or apply stimulation signals to particular cortical regions of the patient's brain 192 and/or neural populations synaptically connected and/or proximate thereto. A cortical electrode 142 may include one or more electrically conductive contacts 144 carried by a substrate 146, for example, in a manner described in U.S. application Ser. No. 10/742,579, entitled "Methods and Apparatus for Applying Electrical Stimulation and Manufacturing Same," filed on Dec. 18, 2003, which is incorporated herein by reference. The set of electrodes 140 may alternatively or additionally include one or more penetrating, depth, deep brain, and/or nerve cuff electrodes. The set of electrodes 140 may further include or provide one or more stimulation signal return electrodes (i.e., electrodes that provide a current return path or electrical continuity) that may be positioned relative to a variety of locations within and/or upon the patient's body, and which may facilitate unipolar stimulation.

The characteristics and/or placement of the set of electrodes 140 may depend upon the nature of patient's underlying disorder(s), functional deficit(s), and/or the type and/or severity of symptoms that the patient 190 experiences or exhibits. In one embodiment, one or more portions of the set of electrodes 140 may be surgically implanted to apply, deliver, and/or direct stimulation signals to target neural populations within the patient's brain, for example, in a manner identical, essentially identical, or analogous to that described in U.S. application Ser. No. 10/732,731, entitled "System and Method for Treating Parkinson's Disease and Other Movement Disorders," filed on Dec. 9, 2003, incorporated herein by reference; and/or U.S. application Ser. No. 09/802,808.

The pulse generator 110a may comprise hardware and/or software for generating and outputting stimulation signals to the set of electrodes 140 in accordance with internal instruction sequences and/or in response to control signals, commands, instructions, and/or other information received from a programming unit 160, 161. The pulse generator 110a may include a power supply, a pulse unit, a control unit, a programmable computer medium, and a communication unit. The power supply may comprise a battery or other type of power storage device. The pulse unit may comprise circuitry for generating pulse sequences that may be defined or characterized in accordance with various stimulation signal parameters, which are further described below with reference to FIG. 2.

The control unit may comprise hardware and/or software configured to direct or manage the local operation of the pulse generator 110a. The communication unit may comprise a user interface that facilitates communication with devices external to the pulse generator 110a, for example, through telemetric signal transfer. The programmable computer medium may comprise hardware and/or memory resident software. The programmable computer medium may store operational mode information and/or program instruction sequences that may be selected and/or specified in accordance with information received from the programming unit 160. The pulse generator 110a may be configured to deliver stimulation signals to particular electrodes 142 and/or specific electrical contacts 144 within the set of electrodes 140 on a selective basis at any given time, possibly in a manner identical, essentially identical, or analogous to that described in U.S. application Ser. No. 09/978,134, entitled "Systems and Methods for Automatically Optimizing Stimulation Parameters and Electrode Configurations for Neuro-Stimulators," filed on Oct. 15, 2001, incorporated herein by reference.

Each element of the pulse generator 110a may be incorporated or embedded into a surgically implantable case or housing. Depending upon embodiment details, the pulse generator 110a may be surgically implanted into the patient 190 in a subclavicular location. Alternatively, a pulse generator 110b may be surgically implanted above the patient's neck, for example, in a skull location posterior to the patient's ear and/or proximate to an electrode implantation site. A surgically formed tunnel or path may route the set of leads 112 that couple the pulse generator 110a, 110b to the set of electrodes 140, in a manner understood by those skilled in the art. Additionally, one or more electrically conductive portions of the pulse generator's case or housing may serve as a return electrode for electrical current.

A programming unit 160, 161 may comprise a device configured to communicate control signals, commands, instructions, parameter settings and/or ranges, and/or other information to the pulse generator 110a. A programming unit 160, 161 may additionally be configured to receive information from the pulse generator 110a. Communication between the programming unit 160, 161 and the pulse generator 110a may facilitate or effectuate specification, selection, and/or identification of operational modes, instruction sequences, and/or procedures for treating one or more patient conditions, states, and/or symptoms associated with PD, other movement disorders, and/or other types of neurologic dysfunction in a variety of manners, including those described in detail below with reference to FIGS. 3 through 11. In certain embodiments, a system 100 may include a full functionality programming unit 160 configured for operation by a medical professional; and a limited or partial functionality programming unit 161 configured for operation by a patient. A partial functionality programming unit 161 may facilitate patient-based selection and/or adjustment of particular preprogrammed operating modes and/or neural stimulation settings. In some embodiments, a full functionality programming unit 160 and a partial functionality programming unit 161 may be configured for wire-based or wireless communication with each other.

In one embodiment, a programming unit 160, 161 includes a processing unit 162, a programmable computer medium 164, and a communication unit 166. The programmable computer medium 164 may store an operating system, program instructions, and/or data, and may comprise various types of hardware and memory resident software, including volatile and/or nonvolatile memory as well as one or more data storage devices. The communication unit 166 may include a wire-based and/or wireless telemetry interface 170 that employs magnetic, radio frequency (RF), and/or optical signaling techniques to communicate with the pulse generator 110a. The communication unit 166 may additionally or alternatively include one or more wire-based and/or wireless interfaces that facilitate communication with other devices such as a computer.

A patient monitoring unit 180 may comprise essentially any type of device, device configuration, subsystem, and/or system configured to detect, monitor, indicate, estimate, characterize, measure, calculate, and/or assess neural pathway characteristics and/or the nature, level, intensity, magnitude and/or severity of one or more types of patient states, conditions, deficits, and/or symptoms associated with PD and/or other neurological dysfunction. For example, a patient monitoring unit 180 may comprise a motion detection system configured to detect patient movement associated with tremor. A motion detection system may include light emitting and/or detecting devices and/or accelerometers coupled to particular patient extremities. As another example, a patient monitoring unit 180 may comprise an Electromyography (EMG) system that includes one or more sets of surface or depth electrodes positioned relative to particular muscle groups for detecting electrical signals corresponding to muscle fiber innervation. As another example, a patient monitoring unit 180 may comprise an Electroencephalograpy (EEG), an Electrocorticography (ECOG) system, and/or a Magnetoencephalography (MEG) system. In one embodiment in which a patient monitoring unit 180 may monitor and/or measure electrical neural activity within the patient 190, the patient monitoring unit 180 may comprise one or more portions of a set of electrodes 180, and possibly software and/or hardware (e.g., signal processing software and/or circuitry) within the pulse generator 110a.

As another example, a patient monitoring unit 180 may comprise a neural imaging system, for example, a Magnetic Resonance Imaging (MRI), a functional MRI (fMRI), a Positron Emission Tomography (PET), and/or other type of system. As another example, a patient monitoring unit 180 may comprise one or more electrodes and/or probes (e.g., cerebral bloodflow monitors) positioned upon, proximate, and/or within given target neural populations, and associated hardware and/or software for detecting, presenting, and/or analyzing signals received therefrom.

As yet another example, a patient monitoring unit 180 may comprise one or more of a computer, a graphical user interface, a computer program, and/or a set of patient interface units and/or devices configured to monitor, measure, and/or characterize particular types of patient functionality, such as a functional state and/or a response, reaction time, or other characteristic associated with cognition; memory; speech; vision; sensation; and/or muscle activity (e.g., strength and/or force corresponding to one or more muscle groups; and/or range, continuity, smoothness, and/or velocity of active and/or passive motion corresponding to one or more patient muscle groups).

In some embodiments, a patient monitoring unit 180 may comprise one or more devices and/or systems configured to provide electrical and/or magnetic stimulation to the patient 190, for example, a Transcranial Magnetic Stimulation (TMS) system and/or one or more portions of a set of electrodes 140. Such devices may facilitate measurement or assessment of particular types of patient state information, such as motor evoked potentials, coherence, cortical and/or other silent periods, and/or other information that may be useful for characterizing neural pathways and/or neural signal propagation, as further described below. In certain embodiments, a patient monitoring unit 180 may be configured for communication with a programming unit 160.

In the context of various embodiments of the invention, patient state information may comprise signals, data, and/or information that measures, indicates, corresponds, and/or generally corresponds to neural pathway characteristics and/or a significance, extent, level, magnitude, intensity, and/or severity of one or more types of patient states, conditions, dysfunction, deficits, and/or symptoms. Patient state information may be generated as a result of human observation, and/or may be acquired, measured, and/or recorded by one or more patient monitoring units 180. Patient state information may additionally or alternatively be derived or calculated based upon a) observation data; b) acquired, measured, and/or recorded signals; and/or c) one or more types of mathematical procedures or operations involving such data and/or signals (e.g., an analog to digital conversion procedure, a filtering procedure, a squaring procedure, an averaging procedure, a transform procedure, a statistical analysis procedure, a spectral analysis procedure, and/or another type of procedure).

Patient state information may comprise and/or be based upon one or more types of electrophysiological signals such as EMG, EEG, ECOG, EMG, evoked potential, and/or other signals. Patient state information may additionally or alternatively comprise and/or be based upon one or more types of functional or behavioral correlate signals and/or behavioral assessment data. Functional or behavioral correlate signals may comprise, for example, accelerometer signals, force and/or strain gauge signals, data and/or results corresponding to tests of patient performance or capability, and/or other types of signals.

In certain embodiments, patient state information may comprise coherence information. Coherence may provide a measure of rhythmic or synchronous neural activity that may result from oscillatory signaling behavior associated with various neural pathways or loops. In general, coherence may be defined as a frequency-domain measure of synchronous activity and/or linear association between a first and a second signal. The first and second signals may be identical or different signal types. For example, depending upon embodiment details, a coherence measurement may be based upon two EMG signals; two EEG signals; two ECOG signals; two MEG signals; an EMG signal and an EEG, ECOG, or MEG signal; an EMG, EEG, ECOG, or MEG signal and a functional correlate signal; or two functional correlate signals; or other signal type pairs. In an exemplary embodiment, a coherence measurement may be based upon or originate from simultaneous acquisition, measurement, and/or recording of MEG or EEG signals paired with EMG signals corresponding to a sustained contraction of a patient's wrist extensors or first dorsal interosseous (FDI) muscle. Those skilled in the art will understand that measurement or determination of coherence may involve multiple signal acquisitions, measurements, and/or recordings, potentially separated by quiescent intervals, and possibly mathematical procedures upon such signals, which may comprise for example, filtering, averaging, transform, statistical operations, and spectral analysis operations.

Oscillatory signaling behavior may appear in or correspond to particular frequency bands depending upon the nature of an activity or task that activates and/or drives such behavior, and/or the particular signal pair under consideration. Additionally, an extent to which oscillatory signaling behavior appears in any given frequency band may correspond to or depend upon the neurophysiological condition of one or more neural populations, projections, subcircuits, pathways, and/or loops involved in such signaling behavior. For example, weak or generally weak tonic muscle contractions may give rise to synchronous oscillations in a frequency band spanning approximately 15 to 30 Hz, typically with a peak energy or intensity centered at approximately 20 Hz in normal, healthy, symptom-free, generally symptom-free, or symptom-controlled individuals. Strong contractions may give rise to synchronous oscillations in a frequency band spanning approximately 30 to 60 Hz, typically with a peak energy or intensity centered at approximately 40 Hz in healthy, symptom-free, generally symptom-free, or symptom-controlled patients. Rhythmic or synchronous oscillations such as those described above may be absent, significantly diminished, or diminished in patients 190 experiencing one or more symptoms or deficits associated with Parkinson's Disease, other movement disorders, and/or other types of neurologic dysfunction. One or more other frequency bands (e.g., a frequency band spanning approximately 3 to 12 Hz) may also exhibit signal content differences or distinctions between patients 190 experiencing neurologic dysfunction and healthy, symptom-free, generally symptom-free, or symptom-controlled patients.

Particular manners of making and/or interpreting coherence measurements are described in detail in "Defective cortical drive to muscle in Parkinson's disease and its improvement with levodopa," Stephan Salenius et al, *Brain* (2002), Vol. 125, p. 491-500; and "Intermuscular coherence in Parkinson's disease: relatioship to bradykinesia," Peter Brown et al., *NeuroReport*, Vol. 12, No. 11, Aug. 8, 2001.

In certain embodiments, patient state information may comprise silent period information. In general, a silent period may be defined as a temporal interval characterized by a reduced level of neural signaling activity. A silent period may occur spontaneously in association with one or more neural signaling sequences, or in response to a set of stimuli. In various embodiments, one or more stimuli directed toward acquiring, measuring, or recording silent period information may be generated by TMS, and/or possibly electrical stimulation.

A cortical silent period may give rise to motor evoked potentials and/or a corresponding EMG silent period. Thus, in certain embodiments, one or more silent period measurements may involve acquisition, measurement, and/or recording of EMG signals corresponding to one or more muscles or muscle groups, for example, the FDI. Such EMG signals may correspond to voluntary patient contractions and/or movements, and/or patient responses to one or more stimuli such as TMS pulses. Silent period measurements may be performed at increasing stimulus intensity levels to aid characterization, analysis, and/or evaluation of a patient's neurofunctional state.

Relative to healthy, symptom-free, generally symptom-free, and/or symptom-controlled patients, one or more silent periods may be temporally shortened or otherwise distorted in patients experiencing one or more symptoms or deficits associated with Parkinson's Disease, other movement disorders, and/or other types of neurologic dysfunction. Particular manners of making and/or interpreting silent period measurements are described in detail in "Applications of Transcranial Magnetic Stimulation in Movement Disorders," Roberto Cantello, *Journal of Clinical Neurophysiology*, Vol. 9, No. 4, 2002; "Cortical and spinal motor excitability during the premovement EMG silent period prior to rapid voluntary movement in humans," Hisashi Aoki et al., *Brain Research*, Vol. 949 (2002), p. 178-187; and "Peripheral silent periods in essential tremor," *Journal of the Neurological Sciences*, Vol. 199 (2002), p. 55-58.

Figure 2:
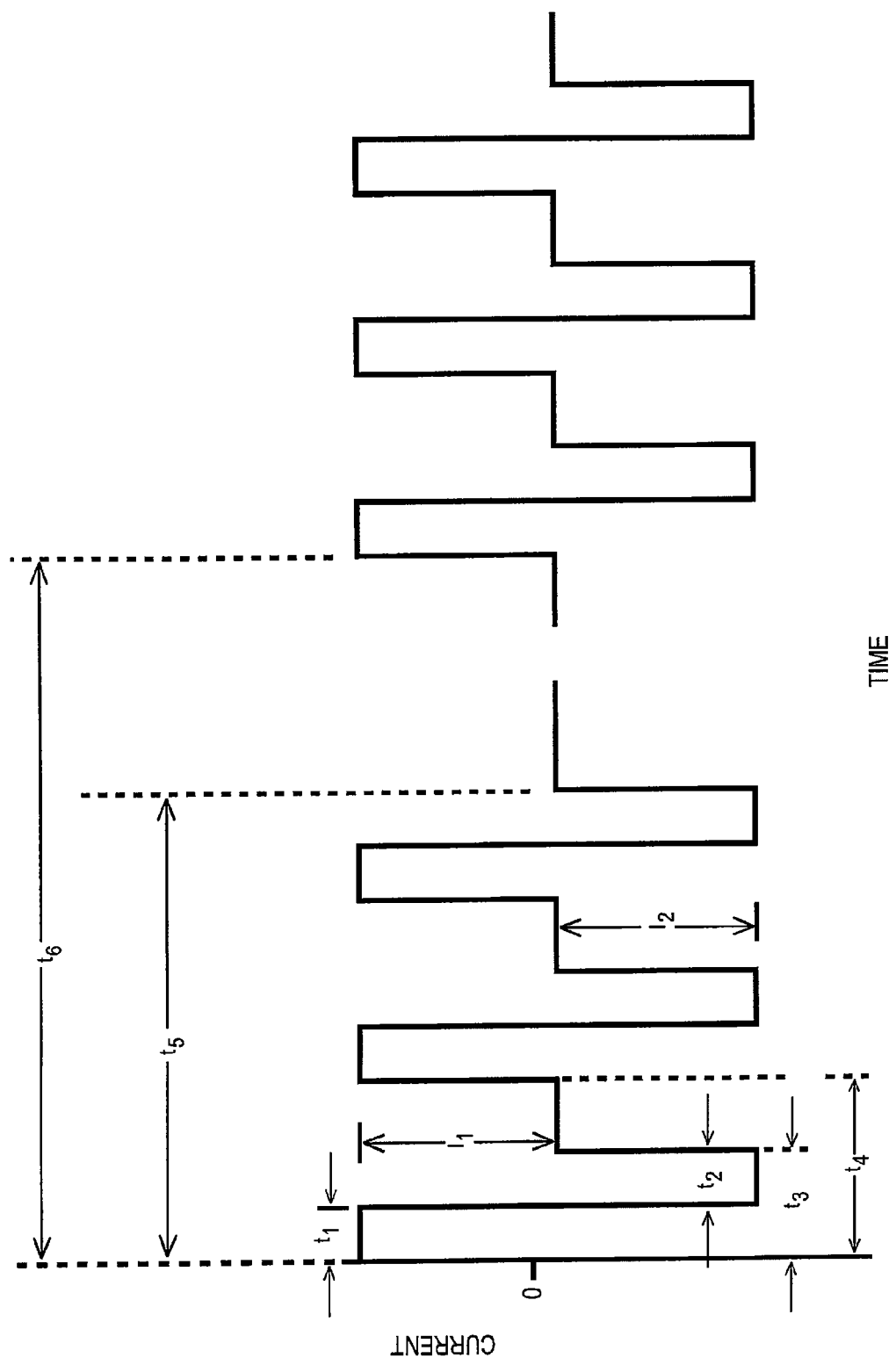
FIG. 2 is a graph illustrating several stimulation parameters that may define, describe, or characterize stimulation signals.

The pulse generator 110a generates and outputs stimulation signals. In the context of the present invention, stimulation signals may comprise electromagnetic pulse sequences. Any given pulse sequence may comprise at least one, and possibly multiple, pulse trains, which may be separated by quiescent intervals. FIG. 2 is a graph illustrating several stimulation parameters that may define, describe, or characterize a pulse train. A stimulus start time to defines an initial point at which a pulse train is applied to one or more elements within the set of electrodes 140. In one embodiment, the pulse train may be a biphasic waveform comprising a series of biphasic pulses, and which may be defined, characterized, or described by parameters including a pulse width $t_1$ for a first pulse phase; a pulse width $t_2$ for a second pulse phase; and a pulse width $t_3$ for one or more biphasic pulses. The parameters can also include a pulse repetition rate $1/t_4$ corresponding to a pulse repetition frequency; a pulse duty cycle equal to $t_3$ divided by $t_4$; a pulse burst time $t_5$ that defines a number of pulses in a pulse train; and/or a pulse train repetition rate $t_6$. Other parameters include a peak current intensity or amplitude $I_1$ for a first pulse phase and a peak current intensity $I_2$ for a second pulse phase.

In various embodiments, the pulse width of successive pulses and/or successive pulse phases may vary, such that the pulse repetition frequency within a pulse train and/or a pulse sequence is a function of time. A pulse train having a frequency that varies in time may give rise to a "chirped" frequency profile. Additionally or alternatively, the pulse intensity or amplitude may decay during the first and/or second pulse phases, and the extent of such decay may differ across successive or subsequent pulse phases. A pulse train may alternatively comprise one or more pseudo-random and/or aperiodic portions, possibly relative to minimum and/or maximum ranges for particular stimulation parameters (e.g., amplitude and/or pulse repetition frequency). Those skilled in the art will understand that a pulse may be a charge-balanced waveform, and that in an alternate embodiment, pulses can be monophasic or polyphasic.

Additional stimulation parameters may specify manners in which pulse trains are applied to selected configurations of elements within the set of electrodes 140, such as particular electrodes 142 and/or contacts 144 and/or signal polarities applied thereto, at any given time.

As defined herein, a test protocol may define or specify neural stimulation parameters associated with one or more pulse sequences to be applied to a patient 190 across or within a given test period duration that may include one or more neural stimulation delivery periods and possibly one or more quiescent periods during which the patient 190 receives no neural stimulation. A test protocol may further define or specify a spatial and/or temporal distribution of elements within the set of electrodes 140 to which neural stimulation may be applied during one or more portions of the test period; and corresponding signal polarities corresponding to particular elements within the set of electrodes 140 relative to one or more portions of the test period. In certain embodiments, a test protocol may additionally specify or indicate one or more types of adjunctive or synergistic therapy (e.g., one or more drug-related therapies) and corresponding adjunctive therapy administration times, and possibly one or more manners of adjusting or modifying neural stimulation based upon an expected or likely adjunctive therapy effect (e.g., an expected drug half-life). Neural stimulation delivered in accordance with a test protocol comprises a test therapy.

Figure 3:
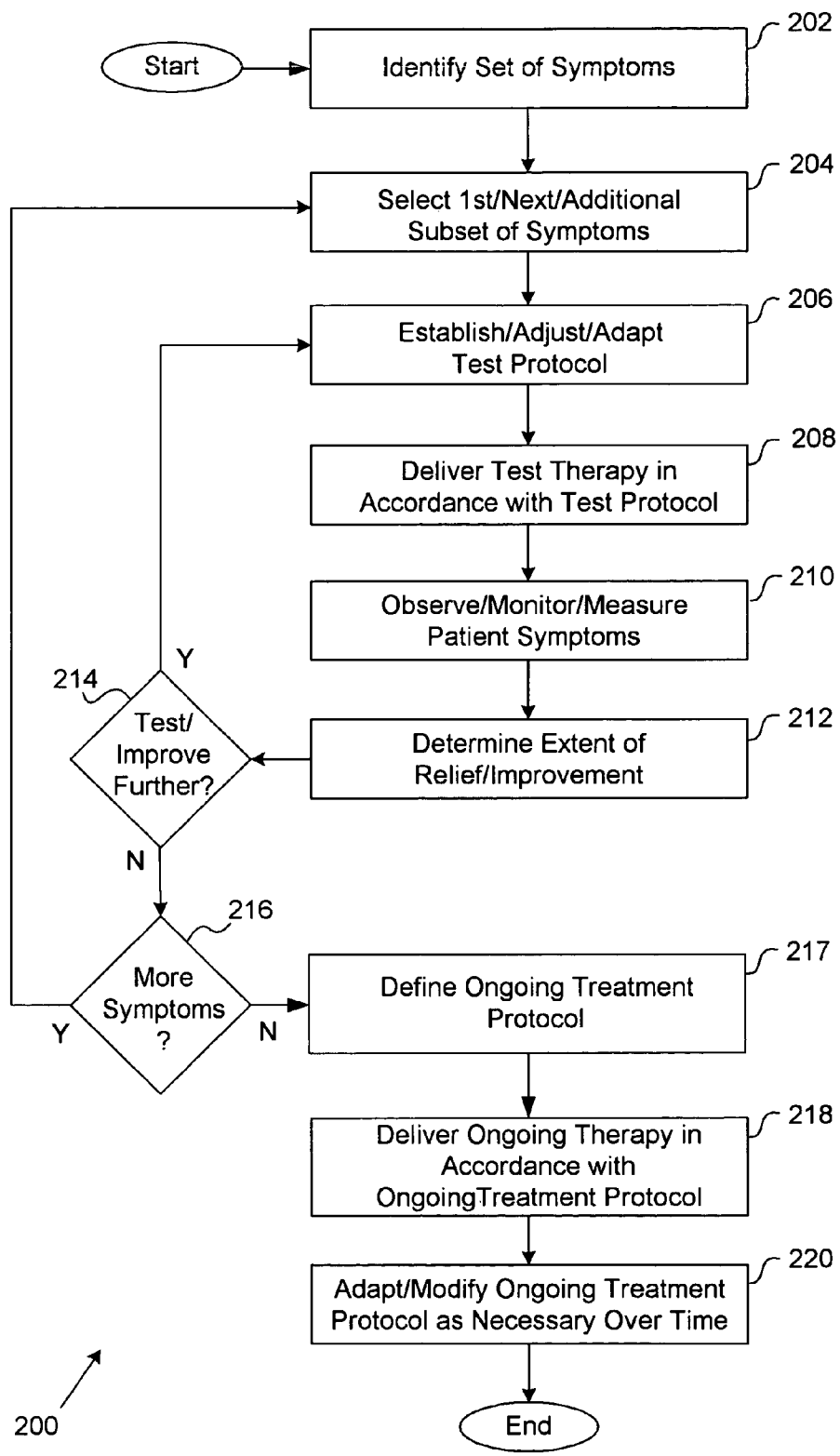
FIG. 3 is a flowchart illustrating various methods for refining, enhancing, or optimizing neural stimulation therapy for treating symptoms of Parkinson's Disease and/or other movement disorders according to an embodiment of the invention.

FIG. 3 is a flowchart illustrating various methods for refining, enhancing, or optimizing neural stimulation therapy for treating symptoms of PD, other neurological disorders, and/or particular types of neurologic dysfunction according to an embodiment of the invention. In some embodiments, a method 200 includes an identification procedure 202 that involves identification of one or more patient symptoms to which neural stimulation therapy, possibly in conjunction with one or more adjunctive therapies, may be directed. Depending upon patient state or condition and/or embodiment details, an adjunctive therapy may comprise a drug-related therapy (e.g., L-dopa therapy, possibly in conjunction with one or more appropriate chemical agonists, uptake inhibitors, neuroprotective agents, and/or other substances). An adjunctive therapy may additionally or alternatively comprise one or more behavioral therapies or tasks (e.g., a physical therapy, an activity of daily living, a cognitive therapy, a memory task, a speech therapy, a visual therapy, and/or another type of therapy or task).

The method 200 may also include a symptom selection procedure 204 that involves selection or consideration of a first, a next, or an additional subset of patient states, conditions, deficits, and/or symptoms to which neural stimulation therapy may be directed. The symptom selection procedure 204 may facilitate initial selection of symptoms expected to rapidly or somewhat rapidly respond to neural stimulation, such as tremor and/or rigidity, followed by selection of other symptoms such as bradykinesia that may respond more slowly.

The method 200 may further include a test protocol management procedure 206 that involves establishing, adjusting, and/or adapting a test protocol that specifies or defines a test therapy intended to be applied to the patient 190 for a given test period. The test protocol may specify or define neural stimulation parameters corresponding to the test therapy, and may also specify parameters corresponding to one or more adjunctive therapies such as a drug-related therapy. The method 200 may additionally include a test delivery procedure 208 that involves application or delivery of the test therapy to the patient 190 in accordance with the test protocol; and an observation procedure 210 that may involve observation, estimation, characterization, monitoring, and/or measuring of patient symptoms and/or patient state information at one or more times in association with and/or following the delivery procedure 208. The observation procedure 210 may involve one or more patient monitoring units 180, and/or direct human observation of the patient 190.

The method 200 may further include an evaluation procedure 212 involving determination of an extent to which one or more patient symptoms or deficits currently under consideration have improved or changed as a result of the most recently applied test therapy. In a manner analogous to that for the observation procedure 210, the evaluation procedure 212 may involve the acquisition, measurement, and/or recording of patient state information by one or more patient monitoring units 180 and/or direct human evaluation of the patient 190 (and/or possibly patient self-evaluation in certain embodiments). The evaluation procedure 212 may further involve analysis of patient state information relative to a therapeutically relevant objective. In the event that additional testing or further improvement of one or more patient states, conditions, deficits, and/or symptoms currently under consideration is necessary, likely, or possible, the method 200 may return to the test protocol management procedure 206. Alternatively, in the event that additional patient symptoms require consideration, the method 200 may return to the symptom selection procedure 204.

In addition to procedures directed toward refining, enhancing, or optimizing an extent to which one or more patient states, conditions, deficits, and/or symptoms can be successfully or adequately treated or managed by neural stimulation (possibly in conjunction with one or more adjunctive therapies), the method 200 may include an ongoing treatment definition procedure 217 that involves defining, establishing, adjusting, and/or updating an ongoing, essentially ongoing, or generally ongoing treatment protocol. An ongoing treatment protocol may specify or indicate one or more manners of treating one or more patient states, conditions, deficits, and/or symptoms over time and/or on an ongoing basis. An ongoing treatment protocol may correspond to or be based upon a previously considered test protocol, and may involve one or more adjunctive therapies. In particular, the ongoing treatment protocol may be identical or essentially identical to a recently considered test protocol, with the exception that an ongoing treatment duration corresponding to the ongoing treatment protocol may be significantly longer than that of the test period corresponding to a test therapy.

Depending upon patient condition and/or embodiment details, an ongoing treatment protocol may include or specify one or more compensatory adjustment procedures directed toward adjusting or modifying neural stimulation parameters (e.g., amplitude, pulse repetition frequency, signal polarity characteristics, and/or other parameters) on a temporary, short term, or periodic basis based upon one or more factors. Such factors may include time of day; patient activity characteristics, activity level or expected patient activity level; and/or an estimated or likely half-life, metabolization, concentration decay, and/or interaction phenomenon corresponding to one or more drugs and/or chemical agents. In one embodiment, if a patient 190 typically retires to bed at a given time (e.g., approximately 10:00 P.M.) on a daily basis, then at a predetermined time and/or during a predetermined time interval (e.g., between 10:30 P.M. and 11:30 P.M.), a compensatory adjustment procedure may modify (e.g., decrease) one or more neural stimulation parameters (e.g., amplitude and/or pulse repetition frequency) in a gradual or predetermined manner until reaching parameter settings appropriate for sleep. A compensatory adjustment procedure may analogously adjust neural stimulation parameters at or shortly prior to an expected patient waking time. In an alternate embodiment, one or more types of neural stimulation parameter adjustment or modification may be triggered (possibly after a given delay time) in response to patient input received from a programming unit 161.

As another example, in the event that a given patient typically receives a drug therapy at 9:00 A.M. daily, and the drug therapy becomes less or significantly less effective approximately 3 hours after drug administration, a compensatory adjustment procedure may specify a transition or increase in stimulation amplitude by a particular amount, for example, 10%; and/or a transition to another pulse repetition frequency beginning at, for example, 11:00 or 11:30 A.M. Additional details pertaining to compensatory adjustment procedures are described below.

The method 200 may additionally include an ongoing treatment delivery procedure 218 that involves application of a determined or an arrived-at ongoing therapy to the patient in accordance with an ongoing treatment protocol. In addition, the method 200 may include a reevaluation procedure 220 that involves a one-time, occasional, or periodic reevaluation, adjustment, and/or adaptation of a most recent ongoing treatment protocol in view of actual, potential, or likely cumulative neurofunctional effects or neuroplastic changes; variations in ongoing treatment effectiveness; and/or overall patient health or condition over time. Such reevaluation, adjustment, or adaptation may occur after a predetermined time interval, such as 1 month, several months, or 1 or more years following initiation of an ongoing treatment delivery procedure 218. The reevaluation procedure 220 may be performed on a one-time or repeated basis based upon the judgment of a medical professional.

The reevaluation procedure 220 may itself involve one or more steps of a method 200. Through a reevaluation procedure 220, it may be determined that one or more patient symptoms may be better, successfully, or adequately treated or managed in accordance with a different pulse repetition frequency function; a lower peak intensity or amplitude; less frequent neural stimulation; a modified configuration of elements within the set of electrodes 140 and/or modified signal polarities applied thereto; lower dosage and/or less frequent drug therapy; and/or other variations in or modifications to the ongoing treatment protocol. As further described below with reference to FIGS. 10 and 11, a reevaluation procedure 220 that indicates that better, successful, or adequate treatment or management of one or more patient symptoms may be achieved with less intense and/or less frequent neural stimulation and/or a lower dosage, less frequent, and/or compositionally altered drug-related therapy or even elimination of one or more drug-related therapies may be indicative of persistent or cumulative neurofunctional effects and/or compensatory, restorative, and/or rehabilitative neuroplastic change within the patient 190.

Figure 4:
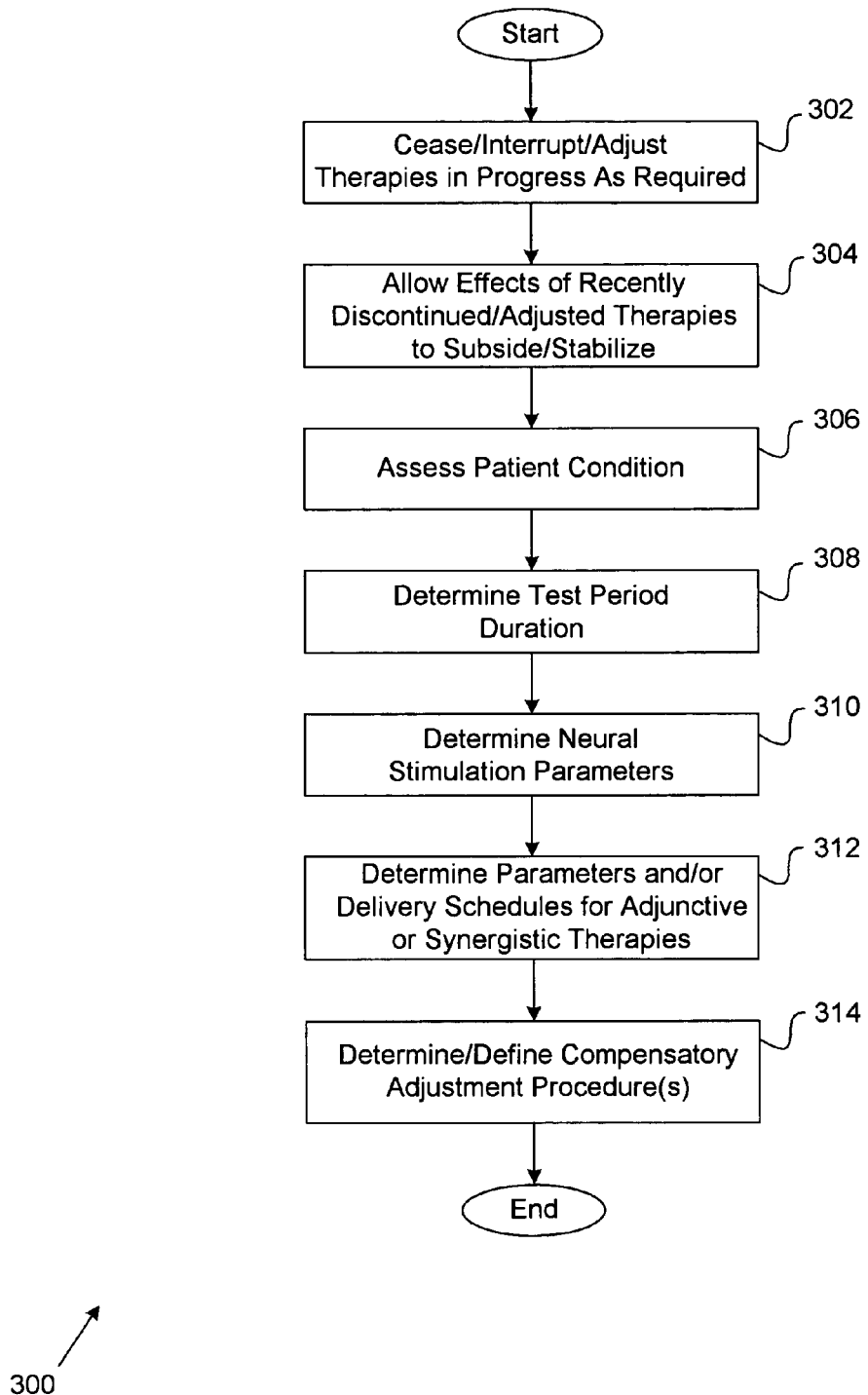
FIG. 4 is a flowchart illustrating various methods for establishing, adjusting, or adapting a test protocol according to an embodiment of the invention.

FIG. 4 is a flowchart illustrating various methods for establishing, adjusting, or adapting a test protocol according to an embodiment of the invention. Such methods may be used in the test protocol management procedure 206 of FIG. 3. In some embodiments, a method 300 includes an adjustment procedure 302 that involves adjustment, cessation, or interruption of patient therapies currently in progress as required. Such therapies may comprise neural stimulation and/or one or more adjunctive therapies such as a drug therapy. The method 300 may also include a waiting procedure 304 during which effects of recently adjusted, discontinued, or interrupted therapies are allowed to subside, stabilize, or "wash out." The waiting procedure 304 may maximize or increase a likelihood that a previously applied therapy has a minimal or negligible effect upon an upcoming test therapy (i.e., no carry-over effects). The method 300 may further include an assessment procedure 306 that involves assessment, qualification, and/or quantification of the severity of one or more patient symptoms, possibly to establish a baseline or reference patient condition.

The method 300 may additionally include a duration establishment procedure 308 that involves determination or definition of a test period duration during which a test therapy may be applied to the patient 190. A test period duration may be short or relatively short, for example, approximately 1 or more minutes or hours, to facilitate efficient determination of the effectiveness of a test protocol upon acute or readily responsive patient symptoms. Alternatively, a test period duration may be relatively long, for example, approximately 1 or more days, weeks, or even months, to facilitate determination of the effectiveness of a test protocol upon patient symptoms having slower or prolonged treatment response characteristics. The method 300 may further include a first test protocol definition procedure 310 that involves determination, selection, and/or specification of neural stimulation parameters that comprise one or more portions of the test protocol. The method 300 may additionally include a second test protocol definition procedure 312 that involves determination or definition of a set of parameters corresponding to one or more adjunctive therapies that may form a portion of the test protocol. Such parameters may include, for example, a drug dosage and delivery schedule. In certain embodiments, the method 300 may also include a compensatory adjustment definition procedure 314 that involves specification of one or more manners in which neural stimulation may be adjusted, modified, varied, and/or modulated in view of a set of adjunctive therapies corresponding to the second test protocol definition procedure 312.

Figure 5:
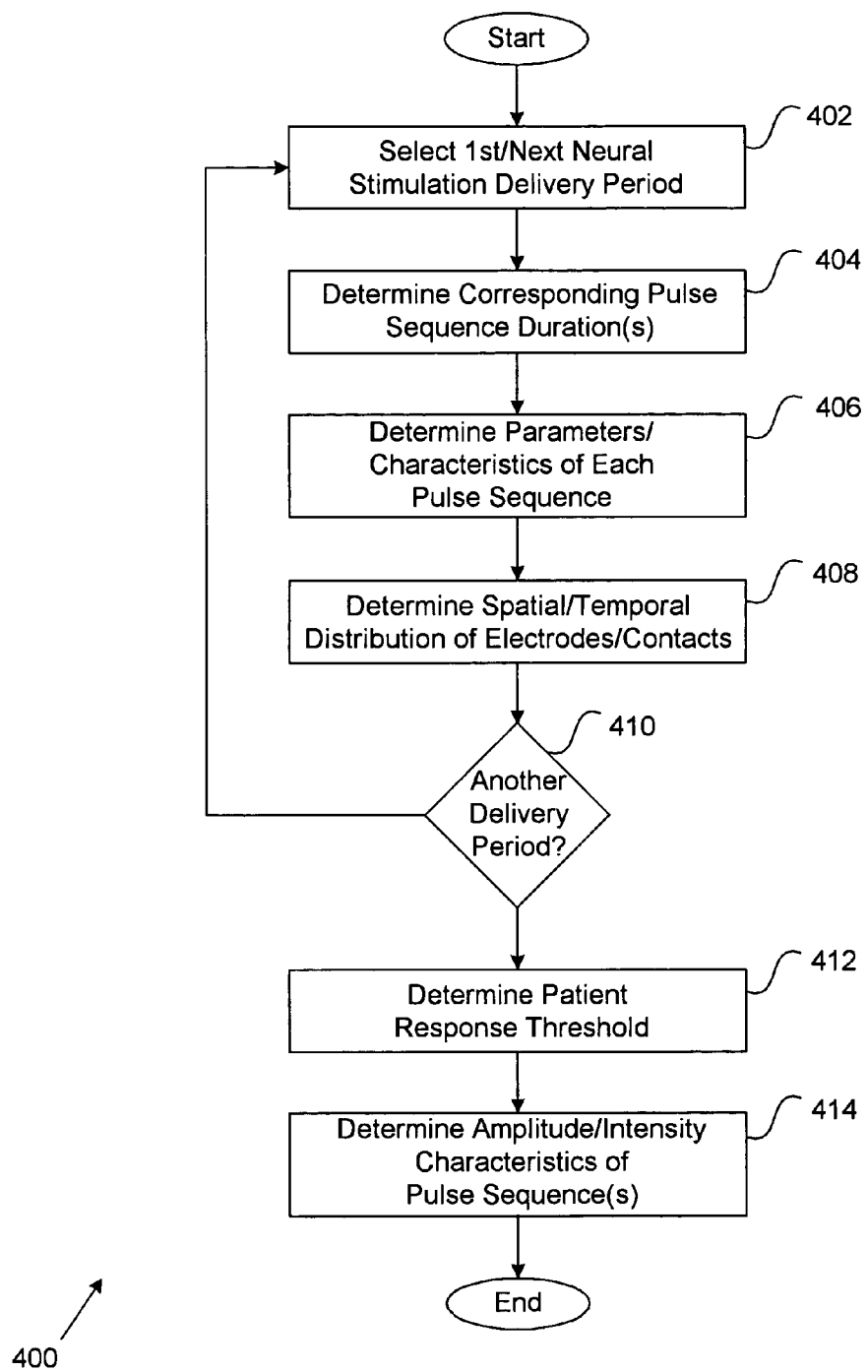
FIG. 5 is a flowchart illustrating various methods for determining neural stimulation parameters according to an embodiment of the invention.

FIG. 5 is a flowchart illustrating various methods for determining neural stimulation parameters according to an embodiment of the invention. Such methods may be used in the first test protocol definition procedure 310 of FIG. 4. In some embodiments, a method 400 includes a delivery period selection procedure 402 that involves determination or selection of a first or next time interval within the current test period that neural stimulation may be delivered to the patient 190. The method 400 may further include a pulse sequence duration procedure 404 that involves selection and/or specification of one or more pulse sequence durations and/or quiescent intervals within and/or between pulse sequences for the neural stimulation delivery period currently under consideration. The method 400 may accommodate multiple pulse sequences, variable types of pulse train sequences, and/or quiescent intervals between pulse sequences to provide enhanced flexibility with respect to establishing test protocols that may be useful for efficiently treating symptoms of various disorders.

Relative to treating PD symptoms, stimulation that reduces the output activity of the globus pallidus internalis (GPi) can be highly beneficial. Deep Brain Stimulation (DBS) research has shown that stimulation delivered to the globus pallidus internalis (GPi) may significantly reduce GPi activity over a period that can last several seconds beyond the termination of such stimulation. For example, a continuous or essentially continuous pulse train lasting 3 seconds may result in reduced or significantly reduced GPi output activity that lasts approximately 1.5 seconds beyond termination of the 3 second pulse train. Delivering or applying neural stimulation to one or more target neural populations having synaptic projections into the GPi or associated neural circuitry such that pulse sequences or pulse trains are separated by one or more appropriate quiescent intervals may therefore maintain or sustain reduced GPi activity while eliminating the need to deliver continuous stimulation. Delivery of neural stimulation in such a manner advantageously reduces power consumption. Thus, a pulse sequence comprising periodic pulse trains lasting approximately 3 seconds separated by quiescent intervals lasting approximately 1.5 seconds may provide significant therapeutic benefit in a power efficient manner.

The method 400 may additionally include a waveform definition procedure 406 that involves selection and/or specification of a set of waveform parameters that define or describe each pulse sequence currently under consideration. Such waveform characteristics may include a pulse repetition frequency or frequency function, a pulse amplitude decay function, and/or other pulse sequence parameters. Depending upon embodiment details and/or current symptoms under consideration, the pulse repetition frequency may vary within any given pulse sequence, and/or from one pulse sequence to another. By accommodating such variation, the method may facilitate the definition of a test protocol or an arrived-at ongoing treatment protocol that includes multiple pulse repetition frequencies, where particular individual pulse frequencies or pulse frequency subsets may be directed toward maximizing or enhancing the effectiveness of neural stimulation in treating particular PD and/or movement disorder symptoms. As an illustrative example, if (a) a pulse repetition frequency of approximately 25 Hz appears optimal or nearly optimal for treating tremor, (b) a pulse repetition frequency of approximately 30 Hz appears optimal for treating rigidity, and (c) a pulse repetition frequency of approximately 15 Hz appears optimal for treating bradykinesia, then a test protocol or an ongoing treatment protocol may call for neural stimulation that periodically alternates between these pulse repetition frequencies in accordance with given neural stimulation delivery periods and possibly including one or more quiescent periods therebetween. Alternatively, the test protocol or the ongoing treatment protocol may call for neural stimulation that sweeps between 15 and 30 Hz in a continuous or nearly continuous manner.

In general, a test protocol may call for neural stimulation having one or more pulse repetition frequencies specified in accordance with a temporal and/or mathematical function that is based upon individual pulse repetition frequencies determined to be optimal or near-optimal for treating particular subsets of patient symptoms. Such a temporal and/or mathematical function may be based upon the nature and/or severity of such symptoms. For example, if the patient's baseline or reference state indicates that the patient experiences tremor in a significantly more severe manner than bradykinesia, a test protocol may call for neural stimulation in which an amount of time spent delivering stimulation optimized or nearly optimized for treating tremor exceeds an amount of time spent delivering stimulation optimized or nearly optimized for treating bradykinesia. Additionally or alternatively, the test protocol may call for neural stimulation having a frequency function that is weighted or biased relative to individually determined frequencies corresponding to particular symptom subsets. Such a test protocol may call for neural stimulation that delivers, for example, a combined frequency of 27 Hz for treating both tremor and rigidity, as well as a pulse repetition frequency of 15 Hz for treating bradykinesia. Furthermore, a test protocol may call for neural stimulation having a pulse repetition frequency function that depends upon one or more treatment response times associated with particular symptoms, and/or one or more time intervals that relief from particular symptoms persists in the absence of neural stimulation.

The method 400 may further include an electrode element selection procedure 408 that involves identifying or defining a spatial and/or temporal distribution of electrodes 142 and/or contacts 144 to which neural stimulation may be directed during the delivery period under consideration. The electrode element selection procedure 408 may alternatively or additionally select or define signal polarities corresponding to particular electrodes 142 and/or contacts 144 relative to one or more portions of the test period. In the event that a current test period includes more than one delivery period, the method 400 may return to the delivery period selection procedure 402.

The method 400 may also include a threshold determination procedure 412 that involves determination of a minimum or near minimum neural stimulation amplitude or intensity that evokes or induces a given type of patient response, reaction, behavior, and/or sensation. A neural stimulation threshold may be determined by successively applying higher amplitude neural stimulation signals to the patient 190 until an observable or detectable response occurs. Each threshold determination attempt may apply a limited duration neural stimulation signal to the patient 190, for example, a pulse sequence lasting 0.5 seconds, 1 second, 3 seconds, or some other length of time. A waiting, quiescent, or washout period between successive threshold determination attempts, during which the patient 190 receives no neural stimulation, may ensure that each threshold determination attempt is independent or essentially independent of residual effects associated with previously applied signals. A quiescent period may span several seconds to one or more minutes, for example, approximately one minute. In one embodiment, the threshold determination procedure 412 involves determination of a motor, movement, or motion threshold through motion detection techniques and/or visual observation. In another embodiment, the threshold determination procedure 412 may involve determination of an EMG threshold and/or another type of neural stimulation threshold.

The method 400 may further include an amplitude determination procedure 414 that involves determination or selection of peak or average amplitudes or intensities corresponding to the set of pulse sequences defined or specified within the current test period based upon the results or outcome of the threshold determination procedure 412. Depending upon embodiment details, a peak pulse sequence amplitude may be defined as a given percentage of a neural stimulation threshold, for example, 50% of a movement threshold or 70% of an EMG threshold. In some embodiments, different pulse sequences within a delivery period or test period may have different peak amplitudes.

One or more procedures identical, essentially identical, or analogous to those described above with reference to FIGS. 3, 4, and/or 5 may facilitate or effectuate manual, semi-automatic, and/or automatic determination of neural stimulation parameters appropriate for addressing or treating one or more patient states, conditions, and/or symptoms on an initial, temporary, test, and/or ongoing basis.

Figure 6:
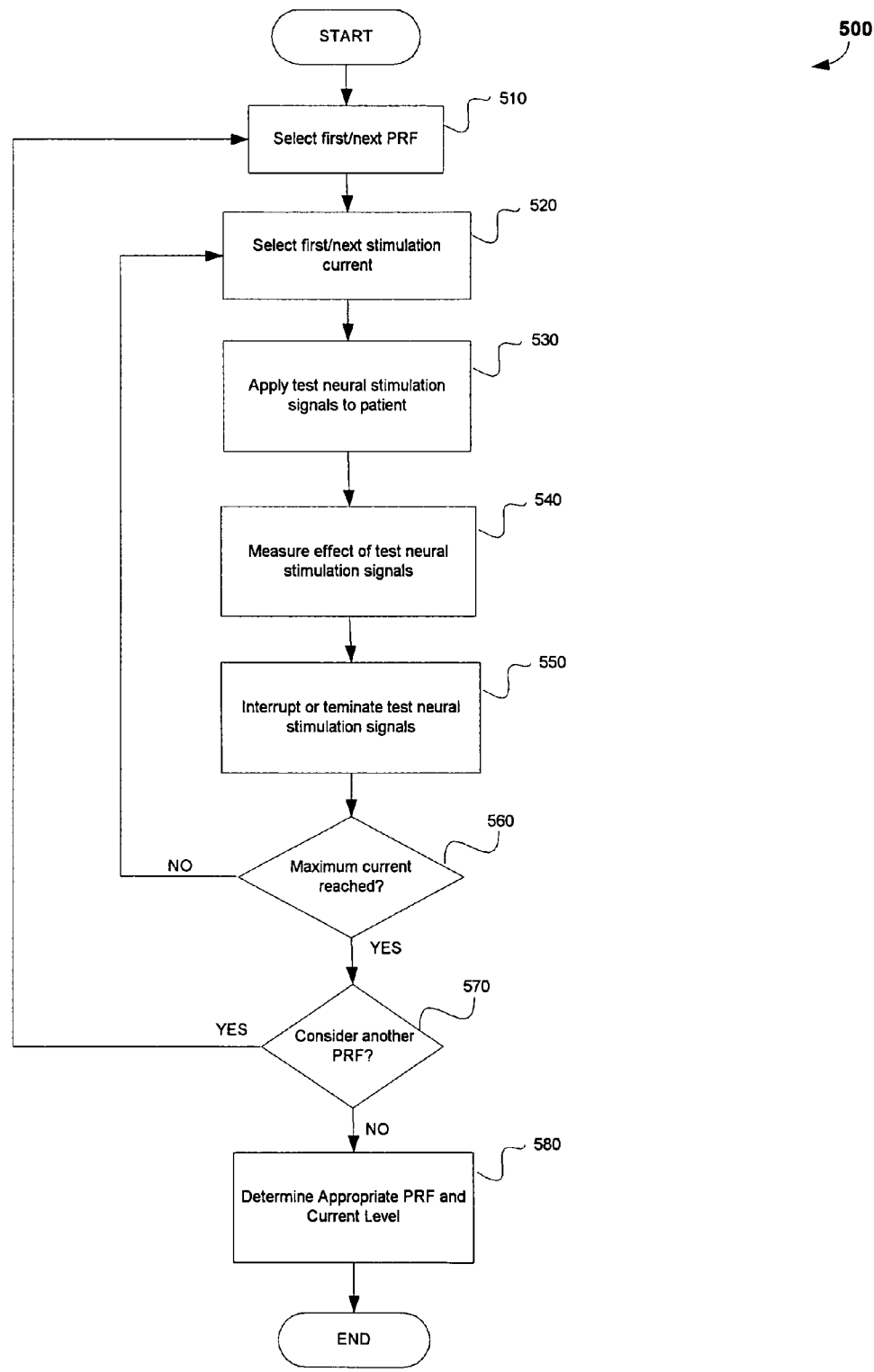
FIG. 6 is a flowchart illustrating various methods for establishing a pulse repetition frequency and/or a stimulation current and/or voltage level expected to be effective or generally effective for addressing or treating particular patient states, conditions, and/or symptoms according to an embodiment of the invention.

FIG. 6 is a flowchart illustrating various methods for establishing a pulse repetition frequency and/or a stimulation current and/or voltage level expected to be effective or generally effective for addressing or treating particular patient states, conditions, and/or symptoms according to an embodiment of the invention. In some embodiments, a method 500 directed toward determining a pulse repetition frequency and a stimulation current level appropriate for treating tremor and rigidity comprises a first selection procedure 510 that involves selecting or establishing a first or next pulse repetition frequency to consider. The method 500 may further comprise a second selection procedure 520 that involves selecting or establishing a first or next stimulation current to consider.

The method 500 may also comprise a stimulation procedure 530 that involves applying test neural stimulation signals to a patient 190 in accordance with a pulse repetition frequency and/or a stimulation current presently under consideration. In one embodiment, the first selection procedure 510 and the second selection procedure 520 initially consider a generally low, low, or very low pulse repetition frequency and stimulation current, respectively, which may reduce or minimize a likelihood of inducing collateral effects (e.g., seizure activity). In certain embodiments, a stimulation procedure 530 may apply test neural stimulation signals to the patient 190 for a predetermined minimum amount of time (e.g., 1 minute, 10 minutes, 30 minutes, or 1 or more hours) and/or maximum amount of time (e.g., 1 minute, 10 minutes, 30 minutes, or 1 or more hours) in the absence of collateral effects.

The method 500 may additionally comprise a stimulation results procedure 540 that involves observing, measuring, recording, classifying, categorizing, comparing, and/or evaluating an effect or apparent effect of the test neural stimulation signals upon the patient 190. Depending upon embodiment details, a stimulation results procedure 540 may involve human observation and/or feedback; and/or detection, measurement, and/or recording of electrophysiological and/or functional correlate signals and/or behavioral assessment data. For example, a stimulation results procedure 540 may involve measurement of one or more coherence and/or silent period signals.

The method 500 may also comprise an interruption procedure 550 that involves interrupting or terminating the application of test neural stimulation signals, and possibly pausing or maintaining a quiescent state for a predetermined minimum amount of time (e.g., 1 minute). The method 500 may additionally comprise a maximum determination procedure 560 that involves determining whether a maximum stimulation current level has been reached. In certain embodiments, a maximum stimulation current level may be reached in the event that the most recently applied test stimulation signals a) evoked a given type of patient response (e.g., a movement threshold); and/or b) reached a predetermined maximum allowable current level (e.g., 6 mA). In certain embodiments, a predetermined maximum allowable current level may be based upon patient condition; a measured or estimated electrode impedance; stimulation device limitations; and/or considerations pertaining to collateral neural activity.

In the event that a maximum stimulation current level has not been reached, the method 500 may return to a second selection procedure 520 to consider another, typically incrementally higher (e.g., by 0.25, 0.50, or 1.0 mA), stimulation intensity, level, or amplitude. If a maximum stimulation amplitude has been reached, the method 500 may return to a first selection procedure 510 to select another pulse repetition frequency. In the event that another pulse repetition frequency is to be considered, the method 500 may return to the first selection procedure 510.

The method 500 may further comprise an evaluation procedure 580 that involves determining a best, expected best, most appropriate, appropriate, and/or adequate pulse repetition frequency and stimulation current level or amplitude with which to treat the patient 190 on an ongoing or generally ongoing basis based upon one or more sets of test neural stimulation results. An evaluation procedure 580 may involve identification, determination, and/or calculation of a stimulation current level that provided a best, most acceptable, and/or most adequate patient effect or result corresponding to any given pulse repetition frequency; and/or a best, most acceptable, and/or most adequate overall patient effect or result across a set of pulse repetition frequencies considered. An evaluation procedure 580 may additionally or alternatively involve acquisition, measurement, and/or recording of patient state information, and/or analysis of patient state information relative to a therapeutically relevant objective. Depending upon embodiment details, an evaluation procedure 580 may determine or select between two or more effective, possibly effective, or apparently appropriate pulse repetition frequency/stimulation current level pairs in accordance with a power consumption target or goal. Depending upon embodiment details, an evaluation procedure 580 may comprise a set of manual, semi-automated, and/or automated procedures or operations.

In certain situations, a patient's treatment status may be defined in accordance with "on" and "off" designations corresponding to a set of therapies that may include a neural stimulation therapy. As used in the following description, in a "therapy 1 status/therapy 2 status" designation, the therapy 1 status corresponds to a drug-related treatment status, and the therapy 2 status corresponds to a neural stimulation treatment status. An "off/off" treatment status may indicate a patient state characterized by an absence or effective absence of drugs and/or particular drug-related effects, as well as an absence of neural stimulation. A treatment status of "on/off" may indicate a patient state characterized by drug-related treatment of one or more patient symptoms, as well as an absence of neural stimulation. Those skilled in the art will understand that a drug-related treatment status of "on" may correspond to a reduction or alleviation of particular patient symptoms, and/or may also correspond to the presence of one or more drug-related side effects (e.g., dyskinesia, swallowing difficulty, cognitive difficulties, and/or other problems). Finally, a treatment status of "off/on" or "on/on" may respectively indicate an "off" or "on" drug-related treatment status as described above, plus the presence or application of neural stimulation.

Figure 7:
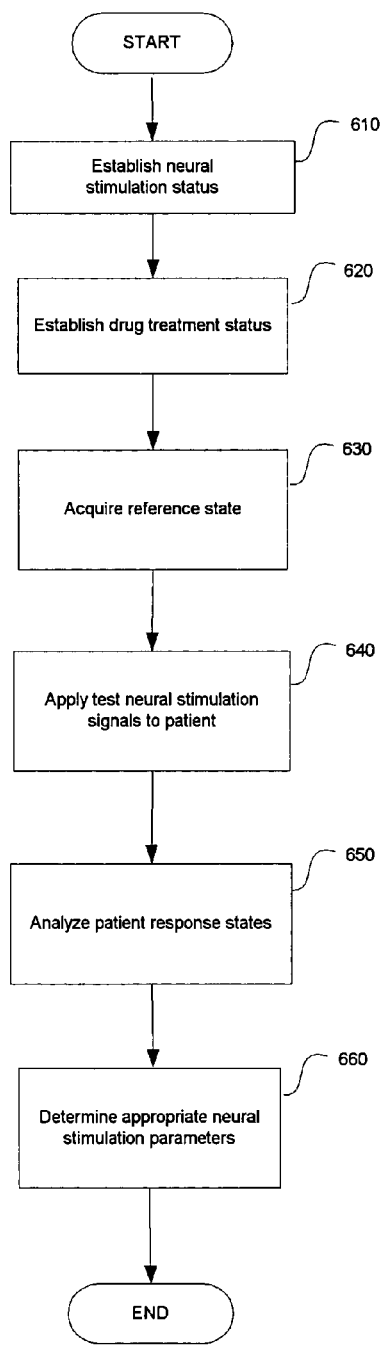
FIG. 7 is a flowchart illustrating various methods for establishing, adjusting, and/or adapting neural stimulation with respect to a drug-related treatment status according to an embodiment of the invention.

FIG. 7 is a flowchart illustrating various methods for establishing, adjusting, and/or adapting neural stimulation with respect to a drug-related treatment status according to an embodiment of the invention. In one embodiment, a method 600 comprises an initial stimulation status procedure 610 that involves establishing a predetermined neural stimulation status, which may typically be an "off" status. The method 600 may further comprise an initial drug status procedure 620 that involves establishing a predetermined drug treatment status, which may be an "on" status or an "off" status depending upon treatment objectives and/or embodiment details. In some embodiments, the initial drug status procedure 620 may establish a drug status of "on" that corresponds to a lower drug and/or associated substance dosage that by itself normally provides the patient 190 with a high, generally high, or acceptable level of symptom control or manageability.

The method 600 may additionally comprise a reference acquisition procedure 630 that may involve acquiring, retrieving, measuring, recording, monitoring, calculating, estimating, characterizing, and/or storing one or more reference, target, and/or comparison states. A reference state may correspond to and/or comprise a set of neural imaging signals, electrophysiological signals, functional correlate signals, and/or signals based thereupon, for example, coherence and/or silent period signals. In certain embodiments, a reference state may additionally or alternatively comprise behavioral assessment data. Depending upon the nature and/or severity of patient symptoms under consideration, treatment objectives, and/or embodiment details, a reference state may correspond to the patient 190 (possibly such that the reference state corresponds to an "on" drug state that by itself generally provides a high, generally high, or acceptable level of symptom control or manageability); one or more individuals having a particular type of deficit, symptom, and/or drug profile; or one or more symptom-free, generally symptom-free, or symptom-controlled individuals.

The method 600 may also comprise a test procedure 640 that involves applying test neural stimulation signals to the patient 190 and acquiring, measuring, recording, monitoring, calculating, estimating, characterizing, and/or storing corresponding patient state information that defines one or more patient response states. A patient response state may correspond to and/or comprise one or more sets of neural imaging signals, electrophysiological signals, functional correlate signals, signals based thereupon, and/or possibly behavioral assessment data.

In certain embodiments, the method 600 may further comprise an analysis procedure 650 that involves analyzing, comparing, evaluating, and/or characterizing a set of patient response states relative to each other and/or one or more reference states. An analysis procedure 600 may involve one or more mathematical operations, functions, transformations, procedures, and/or calculations, possibly including signal processing operations, statistical operations, spectral analysis procedures, and/or other operations.

The method 600 may additionally comprise a determination procedure 660 that involves determining, identifying, or estimating at least one best, expected best, or appropriate set of neural stimulation parameters for treating or affecting one or more patient symptoms under consideration. In certain embodiments, a best, expected best, or appropriate set of neural stimulation parameters may correspond to a closest, most acceptable, or acceptable match between a reference state and a patient response state. An appropriate set of neural stimulation parameters may additionally or alternatively comprise parameters that satisfy a therapeutically relevant objective, for example, parameters that provide a) a largest or most significant silent period increase; b) one or more largest or most significant coherence spectrum shifts approximately within certain frequency bands and/or centered at particular frequencies; and/or c) silent period and/or coherence spectra measurements that most closely resemble symptom-free, generally symptom-free, or symptom-controlled individuals. Depending upon embodiment details, a determination procedure 660 may involve one or more manual, semi-automated, and/or automated procedures or operations.

Figure 8:
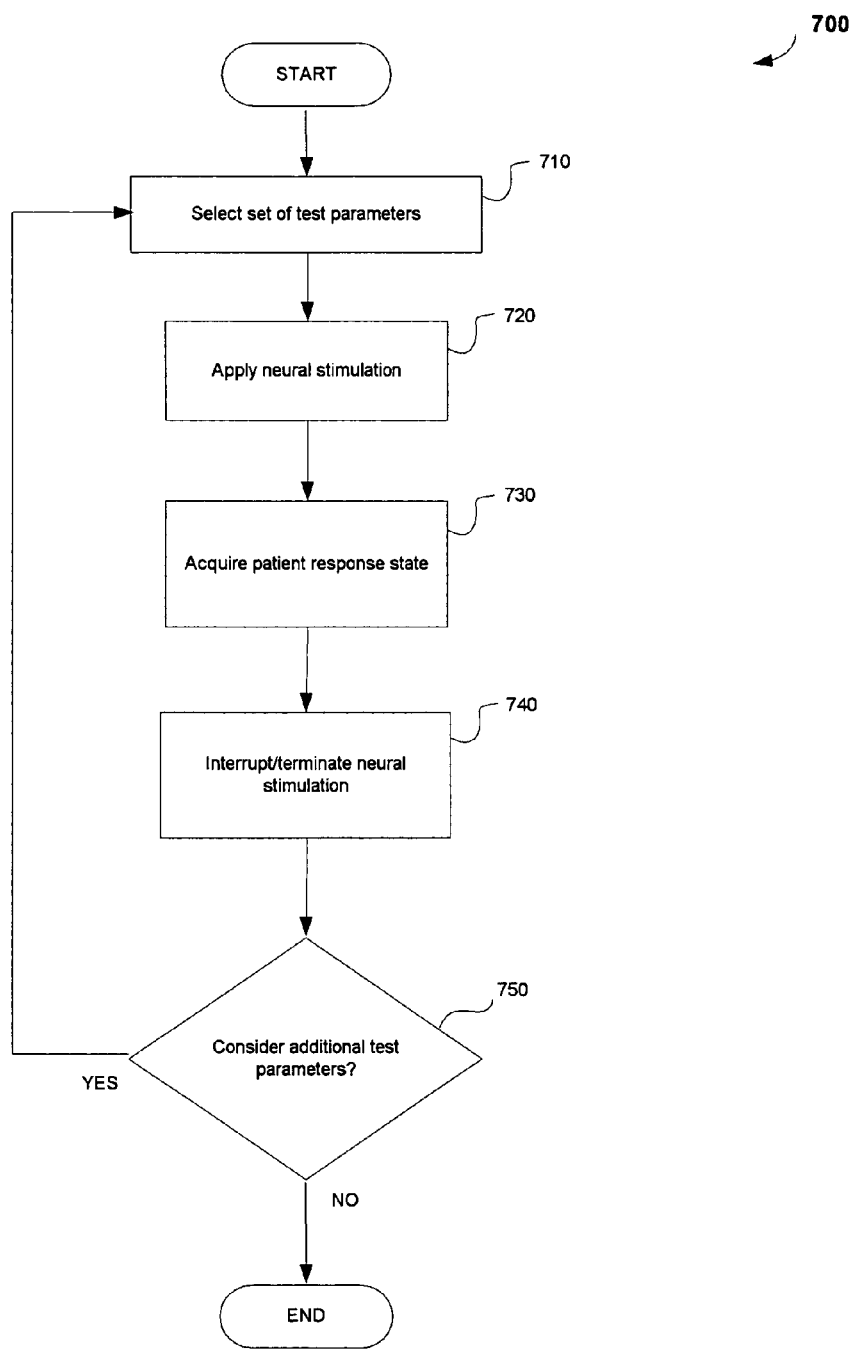
FIG. 8 is a flowchart illustrating various methods for applying test neural stimulation signals to a patient and acquiring one or more corresponding patient response states according to an embodiment of the invention.

FIG. 8 is a flowchart illustrating various methods for applying test neural stimulation signals to a patient 190 and acquiring one or more corresponding patient response states according to an embodiment of the invention. Such methods may correspond to a test procedure 640 of FIG. 7. In some embodiments, a method 700 comprises a parameter selection procedure 710 that involves selecting or establishing a first or next set of test parameters that define or correspond to test neural stimulation signals that the patient 190 is to receive. The method 700 may further comprise a stimulation procedure 720 that involves application of neural stimulation to the patient 190 in accordance with the test parameters presently under consideration. The method 700 may additionally comprise an acquisition procedure 730 that involves acquiring, measuring, monitoring, estimating, characterizing, calculating, and/or storing at least one patient response state. Depending upon embodiment details, an acquisition procedure 730 may involve neural imaging, electrophysiological, and/or functional correlate signals, information derived from or generated using such signals, and/or behavioral assessment data.

In certain embodiments, the method 700 may also comprise an interruption procedure 740 that interrupts, discontinues, or terminates neural stimulation. The interruption procedure 740 may also wait or pause for a given quiescent period (e.g., 1 or more minutes). The method 700 may return to the parameter selection procedure 710 in the event that additional test parameters require consideration; otherwise, the method 700 may end.

During any given day, week, and/or other time period, a number of factors may affect or influence the magnitude, severity, and/or controllability of one or more patient states, conditions, deficits, and/or symptoms. Such factors may include time of day; patient activity type and level; patient emotional state; patient diet; and/or the nature, number, administration schedule, dosage, half-life, and/or administration history of one or more drugs and/or chemical substances.

In certain embodiments, a compensatory adjustment procedure may adjust or modify one or more portions or aspects of a treatment program to accommodate or generally accommodate one or more temporary, short term, or relatively short term symptomatic or functional changes, which may arise in association with one or more factors such as those indicated above. Depending upon embodiment details, one or more compensatory adjustment procedures may be programmed into a pulse generator 110a by a full functionality programming unit 160. In some embodiments, a partial functionality programming unit 161 may facilitate or effectuate patient-based selection, activation, and/or deactivation of one or more compensatory adjustment procedures, and/or patient-based adjustment of particular neural stimulation parameters relative to preprogrammed parameter variability limits.

For example, a patient 190 may periodically perform or attempt to perform an exercise program, a behavioral therapy, and/or a symptomatically relevant behavioral or therapeutic activity on a regular basis (e.g., on a daily basis for approximately 1 or more hours; or 3 times per week for approximately 2 or more hours), and the patient 190 may typically or generally experience symptomatic change (which may comprise symptomatic improvement or deterioration, possibly on a per-symptom basis) for a period of time afterwards (e.g., approximately ½ hour or longer). In such a situation, a compensatory adjustment procedure may adjust or modify neural stimulation for a corresponding or appropriate time period (e.g., adjust neural stimulation amplitude and/or pulse repetition frequency) to facilitate or effectuate accommodation of such change. Initiation and/or termination of a compensatory adjustment procedure may occur at one or more preprogrammed times, and/or in response to patient input received by a programming unit 160, 161. In certain embodiments, transitions between neural stimulation parameters associated with a compensatory adjustment procedure and an ongoing treatment program may be programmed to occur in a gradual, smooth, or stepwise manner.

Figure 9:
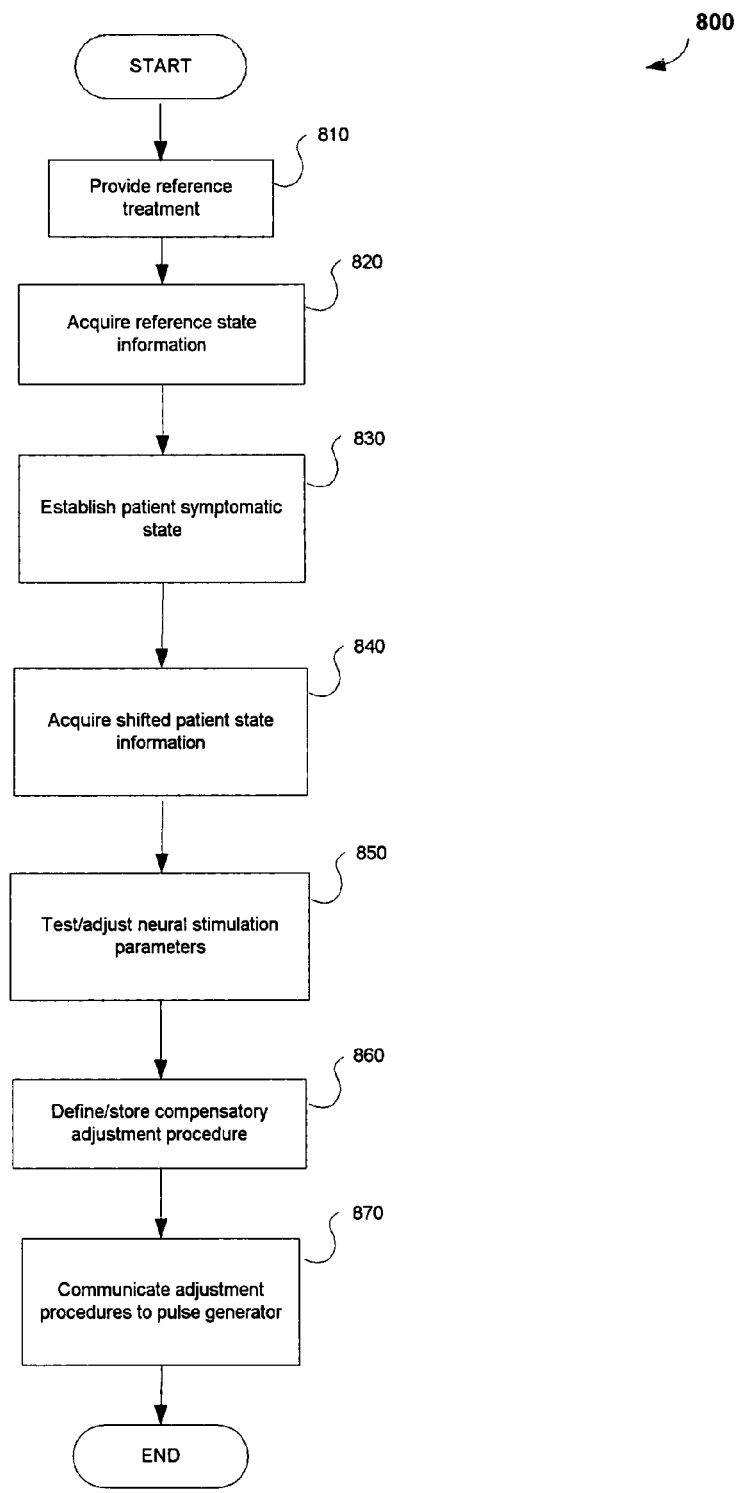
FIG. 9 is a flowchart illustrating various methods for establishing a compensatory adjustment procedure according to an embodiment of the invention.

FIG. 9 is a flowchart illustrating various methods for establishing a compensatory adjustment procedure according to an embodiment of the invention. In some embodiments, a method 800 comprises establishing a reference treatment procedure 810 that involves treating or affecting one or more patient symptoms in a manner that may provide or generally provide a best, expected best, or acceptable degree of overall symptomatic relief or control a majority of the time. A reference treatment procedure 810 may involve applying neural stimulation and possibly one or more drug-related and/or other adjunctive or synergistic therapies to a patient 190 in accordance with an existing treatment program.

In certain embodiments, the method 800 may further comprise a first acquisition procedure 820 that may involve acquiring, measuring, recording, monitoring, observing, estimating, characterizing, calculating, and/or storing reference patient state information. Depending upon embodiment details, the first acquisition procedure 820 may involve neural imaging, electrophysiological, functional correlate, and/or behavioral assessment measurements.

The method 800 may additionally comprise a state establishment procedure 830 that involves establishing or approximately establishing a symptomatic and/or functional state that is identical, essentially identical, or representative of a patient state that typically results in a temporary or short term symptomatic or functional change. A state establishment procedure 830 may involve a drug administration session, a drug level measurement or estimation session, an exercise, activity, or behavioral therapy session, a rest or sleep session, and/or another type of session.

The method 800 may further comprise a second acquisition procedure 840 that may involve acquiring, measuring, recording, monitoring, estimating, characterizing, calculating, and/or storing altered or shifted patient state information corresponding to a temporary or short term symptomatic or functional change. Depending upon embodiment details, the second acquisition procedure 840 may involve neural imaging, electrophysiological, functional correlate, and/or behavioral assessment measurements.

The method 800 may also comprise an adjustment procedure 850 that involves adjusting, adapting, and/or modifying one or more neural stimulation parameters to facilitate and/or effectuate accommodation of or compensation for a temporary symptomatic change. In some embodiments, an adjustment procedure 850 may additionally involve modifying one or more portions of a drug-related or other adjunctive or synergistic therapy. An adjustment procedure 850 may involve applying one or more sets of test neural stimulation signals to the patient 190, and determining a best, appropriate, or adequate set of temporary neural stimulation parameters directed toward addressing a temporary symptomatic change. An adjustment procedure 850 may correspondingly involve acquiring, measuring, recording, monitoring, estimating, characterizing, calculating, and/or storing patient state information, which may include neural imaging, electrophysiological, and/or functional correlate signals and/or behavioral assessment data. Appropriate neural stimulation parameters may be those that a) result in patient state information that is essentially identical, approximately identical, well matched, and/or adequately matched to corresponding reference patient state information; and/or b) satisfy a therapeutically relevant objective. For example, appropriate neural stimulation parameters may be those that most closely approximate normal or nearly normal silent period and/or coherence signal behavior.

In one embodiment, in the event that a temporary symptomatic change involves an improvement in one or more patient symptoms, an adjustment procedure 850 may involve testing one or more sets of test neural stimulation parameters that result in less intense, less frequent, less continuous, and/or reduced power stimulation. In one embodiment, an adjustment procedure 850 may comprise testing stepwise reductions in stimulation amplitude within the context of stepwise reductions in pulse repetition frequency, and identifying a best, appropriate, or adequate pulse repetition frequency and/or stimulation amplitude based upon such testing.

In one embodiment, in the event that a temporary symptomatic change involves a worsening of one or more patient symptoms, an adjustment procedure 850 may involve testing one or more sets of test neural stimulation parameters that result in more intense, more frequent, more continuous, and/or higher power stimulation. An adjustment procedure 850 may comprise testing stepwise increases in stimulation amplitude within the context of stepwise increases in pulse repetition frequency, and identifying a best, appropriate, or adequate pulse repetition frequency and/or stimulation amplitude based upon such testing.

The method 800 may additionally comprise a programming procedure 860 that involves defining and/or storing a compensatory adjustment procedure. Depending upon embodiment details, a compensatory adjustment procedure may be stored upon or within a full functionality programming unit 160, a partial functionality programming unit 161, and/or a remote system or device (e.g., a server, a network attached storage device, a desktop system, and/or a laptop system). The method 800 may further comprise a communication procedure 870 that involves communicating or transferring portions of one or more compensatory adjustment procedures and/or associated information to the patient's pulse generator 110*a*.

Figure 10:
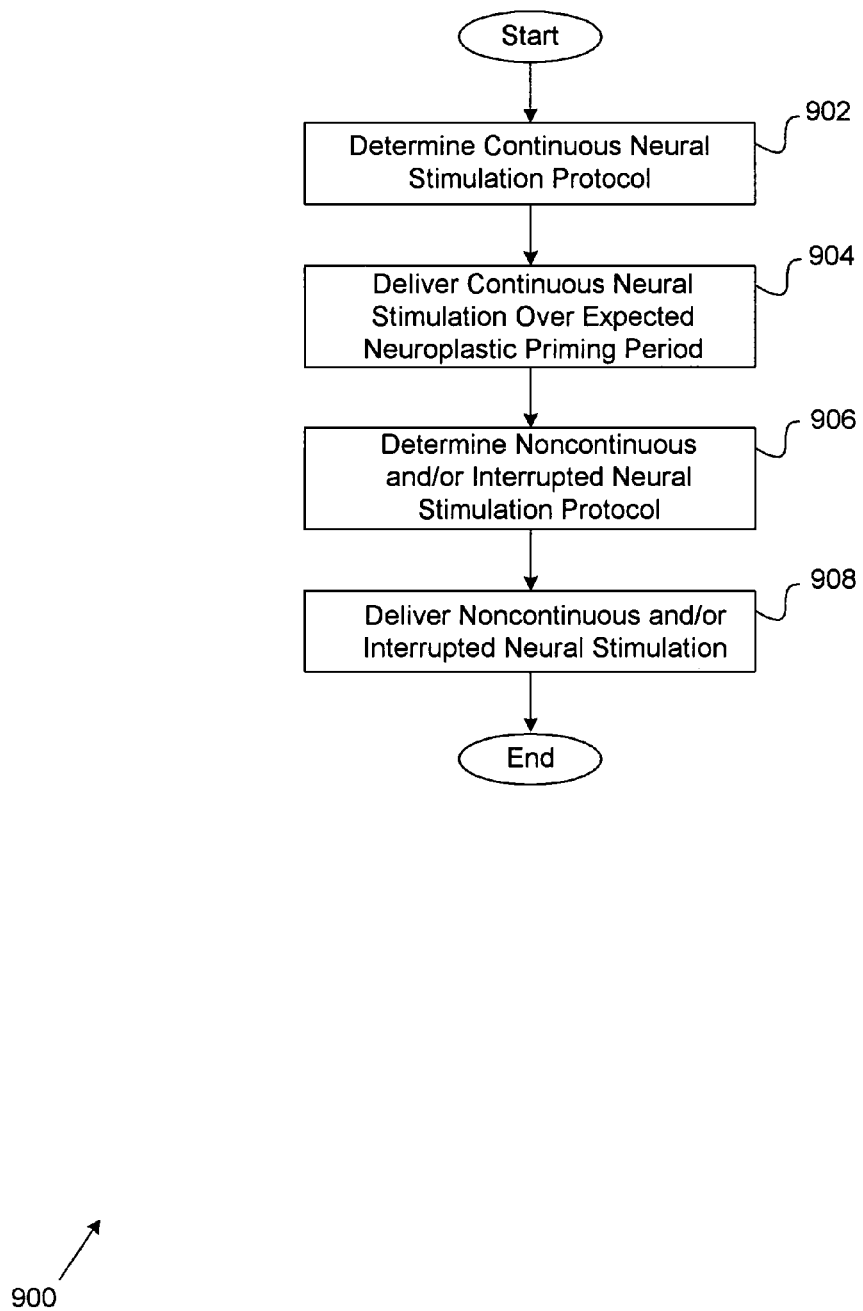
FIG. 10 is a flowchart illustrating various methods for modifying, adjusting, or adapting neural stimulation therapy in view of a likelihood or possibility of a lasting or long term neuroplastic change occurring within a patient over time.

FIG. 10 is a flowchart illustrating various methods for modifying, adjusting, or adapting neural stimulation therapy in view of a likelihood or possibility of a cumulative, persistent, and/or semi-persistent neurofunctional effect and/or a lasting or long term neuroplastic change occurring within a patient 190 over time. Such methods may involve a reevaluation procedure 220 associated with FIG. 3 and/or other procedures described above. The propensity of a given neural population to undergo neuroplastic change may depend upon the application of an initial neural stimulation regimen to the neural population in a particular manner, such as a continuous, generally continuous, or frequent manner over a given or minimum amount of time. This may in turn facilitate or effectuate initiation and reinforcement of chemical and/or structural adaptations or changes in the neural population and/or neural circuitry associated therewith, thereby "priming" the neural population to accept and/or maintain long term or lasting neuroplastic change.

As an illustrative example, depending upon symptom type and severity, effective or generally effective treatment of PD or other movement disorder symptoms may initially require continuous, essentially continuous, or nearly continuous neural stimulation for a neuroplastic priming period of approximately one month. After such a neuroplastic priming period, however, effective treatment of one or more symptoms may require stimulation for a limited number of hours per day, such as during the patient's normal waking hours. Alternatively, effective treatment may require continuous stimulation for approximately 30 minutes, after which treatment may be interrupted for approximately 30 minutes, and so on. In another embodiment, the stimulation can be applied on a twenty-four hour basis for an initial period and then on a reduced basis for a subsequent period. The stimulation, for example, can be applied all throughout each day for an initial period of approximately one month, and then it can be applied only during waking hours after the initial period. This is expected to provide sufficient results in many situations and conserve battery life.

One method 900 for modifying, adjusting, or adapting neural stimulation therapy in view of a likelihood or possibility of a lasting or long term neuroplastic change may include a first stimulation optimization or refinement procedure 902 that involves determination of a continuous neural stimulation protocol for treating one or more patient symptoms. The method 900 may further include a continuous stimulation procedure 904 that involves delivery or application of neural stimulation to the patient 190 in accordance with the continuous neural stimulation protocol for a predetermined time period, for example, one or more weeks or one or more months. The predetermined time period may correspond to an expected or likely neuroplastic priming period. The method 900 may additionally include a second stimulation optimization or refinement procedure 906 that involves determination of a noncontinuous and/or periodically interrupted neural stimulation protocol for treating patient symptoms under consideration. The method 900 may also include a noncontinuous or interrupted stimulation procedure 908 that involves delivery of noncontinuous and/or interrupted neural stimulation to the patient 190 in accordance with the noncontinuous and/or interrupted neural stimulation protocol. The first and/or second stimulation optimization or refinement procedures 902, 906 may include or encompass one or more procedures described above in association with FIG. 3. Additionally, the second stimulation optimization or refinement procedure 906 may be repeated following application of noncontinuous or interrupted stimulation to the patient 190 for a given amount of time.

Figure 11:
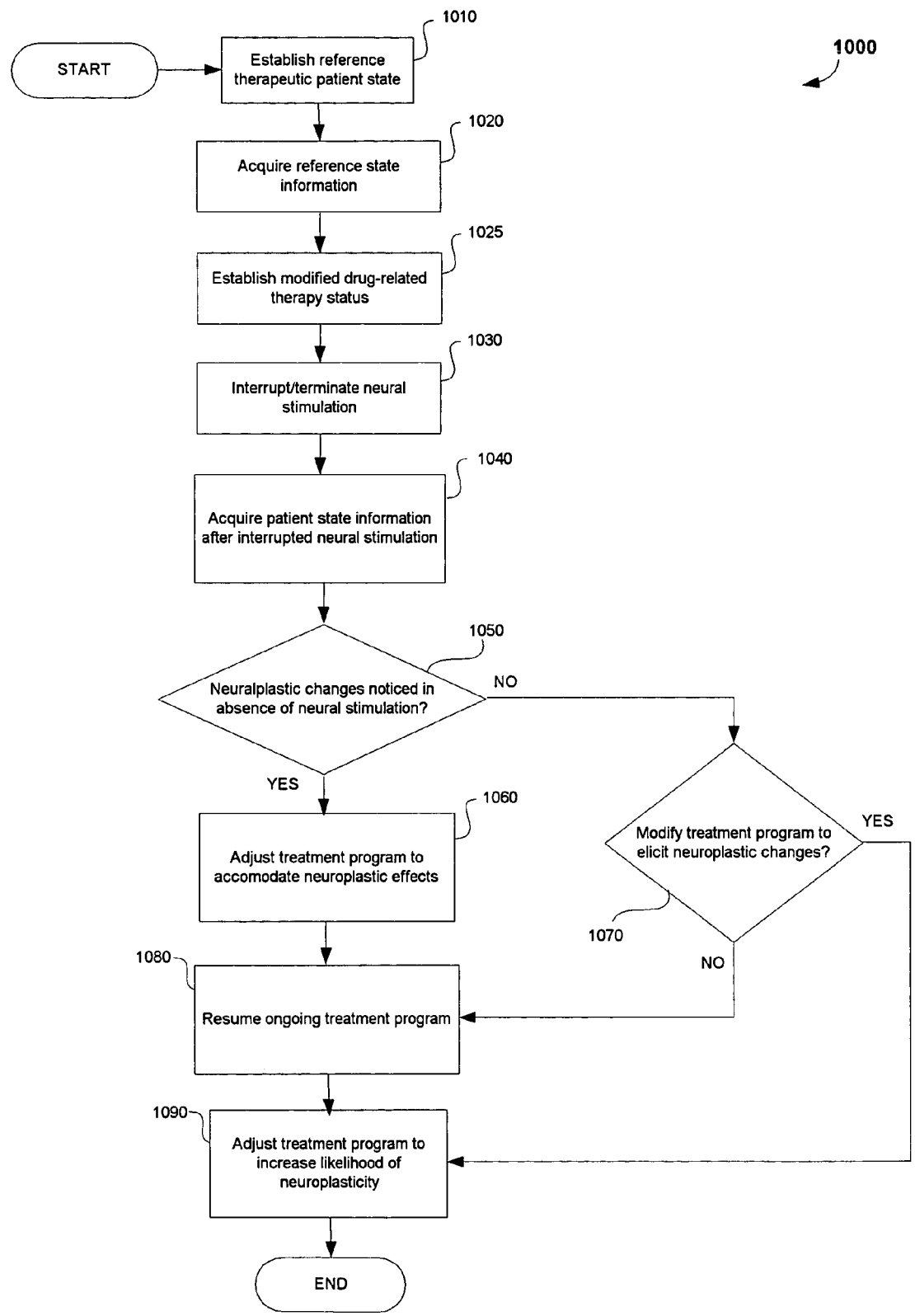
FIG. 11 is a flowchart illustrating various methods for identifying and/or accommodating cumulative, persistent, and/or semipersistent neurofunctional change and/or neuroplastic effects according to an embodiment of the invention.

FIG. 11 is a flowchart illustrating various methods for identifying and/or accommodating cumulative, persistent, and/or semipersistent neurofunctional change and/or neuroplastic effects according to an embodiment of the invention. In some embodiments, a method 1000 may comprise a reference treatment procedure 1010 that involves establishing or approximately establishing a reference therapeutic patient state. In certain embodiments, establishing a reference therapeutic state may involve one or more procedures described above with reference to FIG. 10, and/or treating a patient 190 in accordance with an ongoing treatment program for a given amount of time (e.g., several days, weeks or months). A reference treatment procedure 1010 may involve neural stimulation and possibly one or more drug-related and/or other adjunctive or synergistic therapies. The method 1000 may further comprise a first acquisition procedure 1020 that may involve acquiring, measuring, recording, monitoring, estimating, characterizing, calculating, and/or storing reference patient state information corresponding to a reference therapeutic state.

Depending upon patient condition, the nature and/or extent of a patient's symptoms, deficits, or neurologic dysfunction, patient treatment history, and/or embodiment details, the method 1000 may further comprise a drug or adjunctive state modification procedure 1025 that may involve establishing a modified, altered, or adjusted drug-related and/or other adjunctive therapy treatment status. A modified drug-related treatment status may correspond to a drug "off" status, or a drug "on" status involving one or more drug, drug combination, and/or dosage changes.

The method 1000 may also comprise an interruption procedure 1030 that involves interrupting, discontinuing, or terminating neural stimulation. Additionally, the method 1000 may comprise a second acquisition procedure 1040 that involves acquiring, measuring, monitoring, recording, estimating, characterizing, calculating, and/or storing patient state information after neural stimulation is interrupted or discontinued. The second acquisition procedure 1040 may acquire such information on a one-time, interval-driven or periodic, generally continuous, or continuous basis.

The method 1000 may further comprise an evaluation procedure 1050 that involves determining whether evidence of a cumulative, persistent, or semi-persistent effect and/or neuroplastic change exists in the absence of neural stimulation. In general, such evidence may be indicated the presence of a neurophysiologic, symptomatic, and/or functional state or condition that is sustained or generally maintained for a given amount of time (e.g., approximately several seconds, 1 or more minutes or hours, or possibly longer) after neural stimulation is interrupted or discontinued.

More particularly, such evidence may be indicated by patient state information that exhibits particular types of time dependent behavior, such as patient state information that a) remains constant or unchanging, generally constant, and/or within particular limits for a given period of time; and/or b) changes gradually or generally gradually over time and/or by a maximum allowable extent (e.g., 5% or 10%) over a minimum allowable time interval (e.g., several minutes, at least 1 hour, or approximately 1 or more days) in the absence of neural stimulation. In certain embodiments, the evaluation procedure 1050 may perform mathematical and/or statistical operations that facilitate or effectuate analysis of patient state information over time, possibly relative to reference patient state information. For example, the evaluation procedure 1050 may determine whether a difference, deviation, and/or correlation between reference patient state information and patient state information acquired in the absence of neural stimulation meets one or more criteria at one or more times. In general, the manner in which patient state information behaves relative to time may depend upon patient condition, the nature and/or extent of a patient's neurologic dysfunction, patient treatment history, and/or embodiment details. Evidence of the aforementioned effects and/or changes may exist for several seconds, several minutes, one or more hours, one or more days, one or more months, or essentially on a permanent basis.

In the event that evidence of cumulative effects and/or neuroplastic change exists, the method 1000 may comprise a first adjustment procedure 1060 that involves adjusting, modifying, and/or updating a treatment program to facilitate or effectuate accommodation of such effects and/or changes. In certain embodiments, accommodation of such effects and/or changes may result in less intense, lower frequency, and/or less frequent or more intermittent stimulation, thereby reducing power consumption. Accommodation of such effects and/or changes may additionally or alternatively result in one or more lower drug dosages and/or less frequent drug treatment, which may reduce drug-related side effects and/or extend an amount of time that a patient remains responsive to a drug-related therapy. In various embodiments, a first adjustment procedure 1060 may involve one or more procedures described above, for example, a set of procedures associated with or corresponding to FIG. 3.

In the event that evidence of a cumulative, persistent, and/or semi-persistent effect and/or neuroplastic change is absent, questionable, or minimally existent, the method 1000 may comprise a resumption procedure 1080 that involves resuming or restarting an ongoing treatment program. Alternatively, the method 1000 may comprise a second adjustment procedure 1090 that involves adjusting or modifying a treatment program in a manner that may increase a likelihood that cumulative effects and/or neuroplastic change will result. Depending upon embodiment details, a second adjustment procedure may comprise one or more procedures described above, such as procedures associated with or corresponding to FIGS. 3 and/or 10.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A method comprising:
   applying at least one set of test neural stimulation signals to a patient having a neurologic dysfunction;
   acquiring at least one from the group of a set of coherence measurements and a set of silent period measurements; and
   determining a set of therapeutic neural stimulation parameters directed toward affecting the patient's neurologic dysfunction;
   delivering cortical stimulation to the patient; and
   performing an adjunctive therapy in conjunction with delivering cortical stimulation.

2. The method of claim 1, wherein the set of therapeutic neural stimulation parameters comprises a first subset of neural stimulation parameters directed toward affecting a first patient symptom and a second subset of neural stimulation parameters directed toward affecting a second patient symptom.

3. The method of claim 1, further comprising positioning a set of electrodes with respect to a target neural population within the patient.

4. The method of claim 3, wherein at least one electrode within the set of electrodes is configured to deliver neural stimulation to a cortical region within the patient.

5. The method of claim 4, wherein the cortical region corresponds to a neural population that facilitates a degree of control over at least one type of patient movement.

6. The method of claim 1, wherein delivering cortical stimulation occurs in a manner that increases a likelihood of facilitating or effectuating a lasting neurofunctional change that exhibits a persistent behavior in the absence of neural stimulation.

7. The method of claim 1, further comprising acquiring reference therapeutic state information.

8. The method of claim 7, wherein determining a set of therapeutic stimulation signals comprises evaluating reference therapeutic state information relative to at least one from the group of the set of coherence measurements and the set of silent period measurements.

9. A method comprising:
   establishing a reference treatment state in a patient, the reference treatment state directed toward producing a reference symptomatic state, the reference treatment state established at least partly through delivery of neural stimulation to the patient in accordance with a first set of neural stimulation parameters;
   acquiring reference patient state information corresponding to the reference treatment state, the reference patient state information comprising at least one from the group of a set of coherence measurements and a set of silent period measurements;
   establishing a shifted symptomatic state in the patient;
   acquiring shifted patient state information corresponding to the shifted symptomatic state, the shifted patient state information comprising at least one from the group of a set of coherence measurements and a set of silent period measurements;
   evaluating the shifted patient state information relative to the reference patient state information; and
   determining a second set of neural stimulation parameters directed toward accommodating the shifted symptomatic state.

10. The method of claim 9, wherein the second set of neural stimulation parameters comprises a first subset of neural stimulation parameters directed toward affecting a first patient symptom and a second subset of neural stimulation parameters directed toward affecting a second patient symptom.

11. The method of claim 9, wherein the shifted symptomatic state corresponds to a drug-related condition.

12. The method of claim 9, wherein the shifted symptomatic state corresponds to a drug-related half-life.

13. The method of claim 9, wherein the shifted symptomatic state corresponds to a patient activity.

14. The method of claim 9, wherein the shifted symptomatic state corresponds to a time of day.

15. The method of claim 9, further comprising positioning a set of electrodes with respect to a target neural population within the patient.

16. The method of claim 15, wherein at least one electrode within the set of electrodes in configured to deliver neural stimulation to a cortical region within the patient.

17. The method of claim 9, further comprising delivering cortical stimulation to the patient in accordance with the second set of neural stimulation parameters for a limited time period.

18. The method of claim 17, wherein the limited time period is greater than approximately 1 hour.

19. The method of claim 17, wherein delivering cortical stimulation to the patient in accordance with the second set of neural stimulation parameters occurs on a programmed basis.

20. The method of claim 17, wherein delivering cortical stimulation to the patient in accordance with the second set of neural stimulation parameters occurs in response to a signal communicated by a patient operated device.

21. The method of claim 17, further comprising delivering cortical stimulation to the patient in accordance with the first set of neural stimulation parameters after the limited time period.

22. The method of claim 9, further comprising communicating information corresponding to the second set of neural stimulation parameters to at least one from the group of a programming unit and an implantable pulse generator.

23. A method comprising:
   treating a patient having a neurofunctional deficit in accordance with a treatment program comprising a neural stimulation procedure that corresponds to a first set of neural stimulation parameters;

acquiring at least one from the group of a reference set of coherence measurements and a reference set of silent period measurements;

interrupting a neural stimulation procedure;

acquiring at least one from the group of a comparison set of coherence measurements and a comparison set of silent period measurements; and determining whether evidence of a persistent change corresponding to the patient's neurofunctional deficit exists in the absence of neural stimulation.

24. The method of claim 23, wherein treating a patient occurs over a period of at least one week.

25. The method of claim 23, wherein treating a patient occurs over a period of at least one month.

26. The method of claim 23, wherein treating a patient occurs over a period of approximately one year.

27. The method of claim 23, wherein neural stimulation comprises cortical stimulation.

28. The method of claim 23, wherein the treatment program additionally comprises a drug-related procedure.

29. The method of claim 23, wherein the treatment program additionally comprises a behavioral therapy procedure.

30. The method of claim 23, wherein the treatment program comprises a behavioral therapy procedure in conjunction with a neural stimulation procedure.

31. The method of claim 23, wherein determining whether evidence that a persistent change exists comprises determining whether a change corresponding to the patient's neurofunctional deficit lasts for a duration of approximately one from the group of several seconds, several minutes, one hour, several hours, one day, several days, one month, and several months.

32. The method of claim 23, wherein determining whether a persistent change exists comprises evaluating at least one from the group of the comparison set of coherence measurements and the comparison set of silent period measurements relative to at least one from the group of the reference set of coherence measurements relative to at least one from the group of the reference set of coherence measurements and the reference set of silent period measurements.

33. The method of claim 23, wherein determine whether evidence of a persistent change exists comprises determining whether at least one from the group of the comparison set of coherence measurements and the comparison set of silent period measurements exhibits generally unchanging behavior for a minimum amount of time.

34. The method of claim 23, wherein determining whether evidence of a persistent change exists comprises determining whether at least one from the group of the comparison set of coherence measurements and the comparison set of silent period measurements exhibits a maximum allowable variation during a minimum allowable time interval.

35. The method of claim 23, further comprising interrupting a drug-related procedure.

36. The method of claim 23, further comprising determining a second set of neural stimulation parameters that facilitate accommodation of a persistent change in the patient's neurofunctional deficit.

37. The method of claim 23, further comprising adjusting a drug-related procedure to facilitate accommodation of a persistent change in the patient's neurofunctional deficit.

38. A method comprising:

treating a patient having a neurofunctional deficit in accordance with a treatment program comprising a cortical stimulation procedure corresponding to a first set of neural stimulation parameters;

interrupting cortical stimulation;

determining whether evidence of a persistent change corresponding to the patient's neurofunctional deficit exists in the absence of cortical stimulation; and determining a second set of neural stimulation parameters that facilitate accommodation of a persistent change in the patient's neurofunctional deficit.

39. The method of claim 38 wherein determining whether evidence of persistent change exists includes obtaining coherence measurements from the patient.

40. The method of claim 38 wherein determining whether evidence of persistent change exists includes obtaining patient measurements during a silent period, corresponding to a characteristic of the silent period, of both.

41. The method of claim 38 wherein determining whether evidence of persistent change exists includes detecting patient movement.

42. The method of claim 38 wherein determining whether evidence of persistent change exists includes detecting patient brain activity.

43. The method of claim 38 wherein determining whether evidence of persistent change exists includes detecting a patient response threshold.

44. The method of claim 38 wherein at least one of determining whether evidence of persistent change exists and determining a second set of neural stimulation parameters is performed automatically.

45. The method of claim 38 wherein determining a second set of stimulation parameters includes determining stimulation parameters that are less intense, lower frequency and/or more intermittent than stimulation in accordance with the first set of stimulation parameters.

* * * * *

UNITED STATES PATENT AND TRADEMARK OFFICE
CERTIFICATE OF CORRECTION

PATENT NO. : 7,353,064 B2
APPLICATION NO. : 10/782526
DATED : April 1, 2008
INVENTOR(S) : Gliner et al.

It is certified that error appears in the above-identified patent and that said Letters Patent is hereby corrected as shown below:

On Page 4, item (56), under "Other Publications", in column 2, line 9, delete "http:/www" and insert -- http://www --, therefor.

On Page 4, item (56), under "Other Publications", in column 2, line 49, delete "Repetitve" and insert -- Repetitive --, therefor.

On Page 5, item (56), under "Other Publications", in column 1, line 15, delete "Friedheim" and insert -- Friedhelm --, therefor.

On Page 5, item (56), under "Other Publications", in column 1, line 49, delete "eplieptic" and insert -- epileptic --, therefor.

On Page 5, item (56), under "Other Publications", in column 2, line 33, delete "Afterdischarges" and insert -- After discharges --, therefor.

On Page 5, item (56), under "Other Publications", in column 2, line 45, delete "opographyn" and insert -- topography --, therefor.

On Page 6, item (56), under "Other Publications", in column 1, line 5, delete "development" and insert -- developmental --, therefor.

On Page 6, item (56), under "Other Publications", in column 1, line 54, delete "Brain," and insert -- Brian, --, therefor.

On Page 6, item (56), under "Other Publications", in column 2, line 5, delete "topogrpahy,"" and insert -- topography," --, therefor.

On Page 6, item (56), under "Other Publications", in column 2, line 46, delete "magentic" and insert -- magnetic --, therefor.

On Page 6, item (56), under "Other Publications", in column 2, line 49, delete "contributions" and insert -- contribution --, therefor.

On Page 6, item (56), under "Other Publications", in column 2, line 62, delete "Lobectormy,"" and insert -- Lobectomy," --, therefor.

On Page 7, item (56), under "Other Publications", in column 1, line 3, delete "Rsearch," and insert -- Research, --, therefor.

UNITED STATES PATENT AND TRADEMARK OFFICE
CERTIFICATE OF CORRECTION

PATENT NO.      : 7,353,064 B2
APPLICATION NO. : 10/782526
DATED           : April 1, 2008
INVENTOR(S)     : Gliner et al.

It is certified that error appears in the above-identified patent and that said Letters Patent is hereby corrected as shown below:

On Page 7, item (56), under "Other Publications", in column 1, line 26, delete "temportal lobectormy" and insert -- temporal lobectomy --, therefor.

In the Drawings on Sheet 6 of 11, in Fig. 6, line 1 (Reference numeral 550), delete "teminate" and insert -- terminate --, therefor.

In the Drawings on Sheet 11 of 11, in Fig. 11, line 2 (Reference numeral 1060), delete "accomodate" and insert -- accommodate --, therefor.

In column 7, line 53, delete "Electroencephalograpy" and insert -- Electroencephalography --, therefor.

In column 7, line 53, delete "Electrocorticograpy" and insert -- Electrocorticography --, therefor.

In column 7, line 54, delete "(ECOG)" and insert -- (ECoG) --, therefor.

In column 8, line 51, delete "ECOG," and insert -- ECoG, --, therefor.

In column 9, line 3, delete "ECOG" and insert -- ECoG --, therefor.

In column 9, line 5, delete "ECOG," and insert -- ECoG, --, therefor.

In column 9, line 5, delete "ECOG," and insert -- ECoG, --, therefor.

In column 9, line 56, delete "relatioship" and insert -- relationship --, therefor.

In column 26, line 39, in Claim 16, delete "in" and insert -- is --, therefor.

In column 27, lines 39-40, In Claim 32, after "measurements" delete "relative to at least one from the group of the reference set of coherence measurements".

UNITED STATES PATENT AND TRADEMARK OFFICE
CERTIFICATE OF CORRECTION

PATENT NO. : 7,353,064 B2
APPLICATION NO. : 10/782526
DATED : April 1, 2008
INVENTOR(S) : Gliner et al.

It is certified that error appears in the above-identified patent and that said Letters Patent is hereby corrected as shown below:

In column 27, line 42, in Claim 33, delete "determine" and insert -- determining --, therefor.

In column 28, line 31, in Claim 40, delete "of both." and insert -- or both. --, therefor.

Signed and Sealed this

Eighteenth Day of November, 2008

JON W. DUDAS
*Director of the United States Patent and Trademark Office*